United States Patent

Itsuji

(10) Patent No.: US 9,310,254 B2
(45) Date of Patent: Apr. 12, 2016

(54) APPARATUS FOR ACQUIRING INFORMATION FROM OBJECT TO BE MEASURED AND AQUIRING METHOD THEREFOR

(71) Applicant: CANON KABUSHIKI KAISHA, Tokyo (JP)

(72) Inventor: Takeaki Itsuji, Hiratsuka (JP)

(73) Assignee: Canon Kabushiki Kaisha, Tokyo (JP)

(*) Notice: Subject to any disclaimer, the term of this patent is extended or adjusted under 35 U.S.C. 154(b) by 87 days.

(21) Appl. No.: 14/161,509

(22) Filed: Jan. 22, 2014

(65) Prior Publication Data

US 2014/0209802 A1 Jul. 31, 2014

(30) Foreign Application Priority Data

Jan. 25, 2013 (JP) ................................. 2013-012174

(51) Int. Cl.
*G01J 5/10* (2006.01)
*G01J 3/42* (2006.01)
*G01J 5/08* (2006.01)
*G01N 21/03* (2006.01)
*G01N 21/3586* (2014.01)

(52) U.S. Cl.
CPC .... *G01J 5/10* (2013.01); *G01J 3/42* (2013.01); *G01J 5/0896* (2013.01); *G01N 21/0303* (2013.01); *G01N 21/3586* (2013.01); *G01N 2021/0339* (2013.01); *G01N 2201/023* (2013.01); *G01N 2201/0225* (2013.01)

(58) Field of Classification Search
CPC ..... G01J 5/24; H04N 5/3535; H04N 5/37455; H04N 5/33; H04N 5/378; H04N 5/357; H04N 3/353
See application file for complete search history.

(56) References Cited

U.S. PATENT DOCUMENTS

| | | | | |
|---|---|---|---|---|
| 2005/0087690 A1* | 4/2005 | Usami et al. | ................ | 250/341.1 |
| 2010/0091266 A1* | 4/2010 | Yasuda et al. | ................... | 356/51 |
| 2011/0272579 A1* | 11/2011 | Itsuji | ........................... | 250/338.1 |
| 2013/0088590 A1* | 4/2013 | Shimura et al. | ............... | 348/135 |
| 2013/0120584 A1* | 5/2013 | Nakayama | ..................... | 348/164 |

FOREIGN PATENT DOCUMENTS

| | | |
|---|---|---|
| JP | 2012047462 A | 9/2013 |
| WO | 03058212 A1 | 7/2003 |
| WO | WO 2012014727 A1 * | 2/2012 ............... H04N 5/33 |

* cited by examiner

*Primary Examiner* — David Porta
*Assistant Examiner* — Jeremy S Valentiner
(74) *Attorney, Agent, or Firm* — Canon USA Inc. IP Division

(57) ABSTRACT

An apparatus configured to acquire information on an object to be measured by an electromagnetic wave pulse, the apparatus includes: a generating unit configured to generate the electromagnetic wave pulse with which the object to be measured is irradiated; a detecting unit configured to detect the electromagnetic wave pulse from the object to be measured; a casing including at least a part of a propagation path of the electromagnetic wave pulse leading from the generating unit to the detecting unit; and a measuring window unit configured to change a propagation distance of the electromagnetic wave pulse by moving a measuring window disposed in a part of the casing. The object to be measured is disposed on an opposite side of the propagation path of the electromagnetic wave pulse inside the casing by interposing the measuring window.

15 Claims, 13 Drawing Sheets

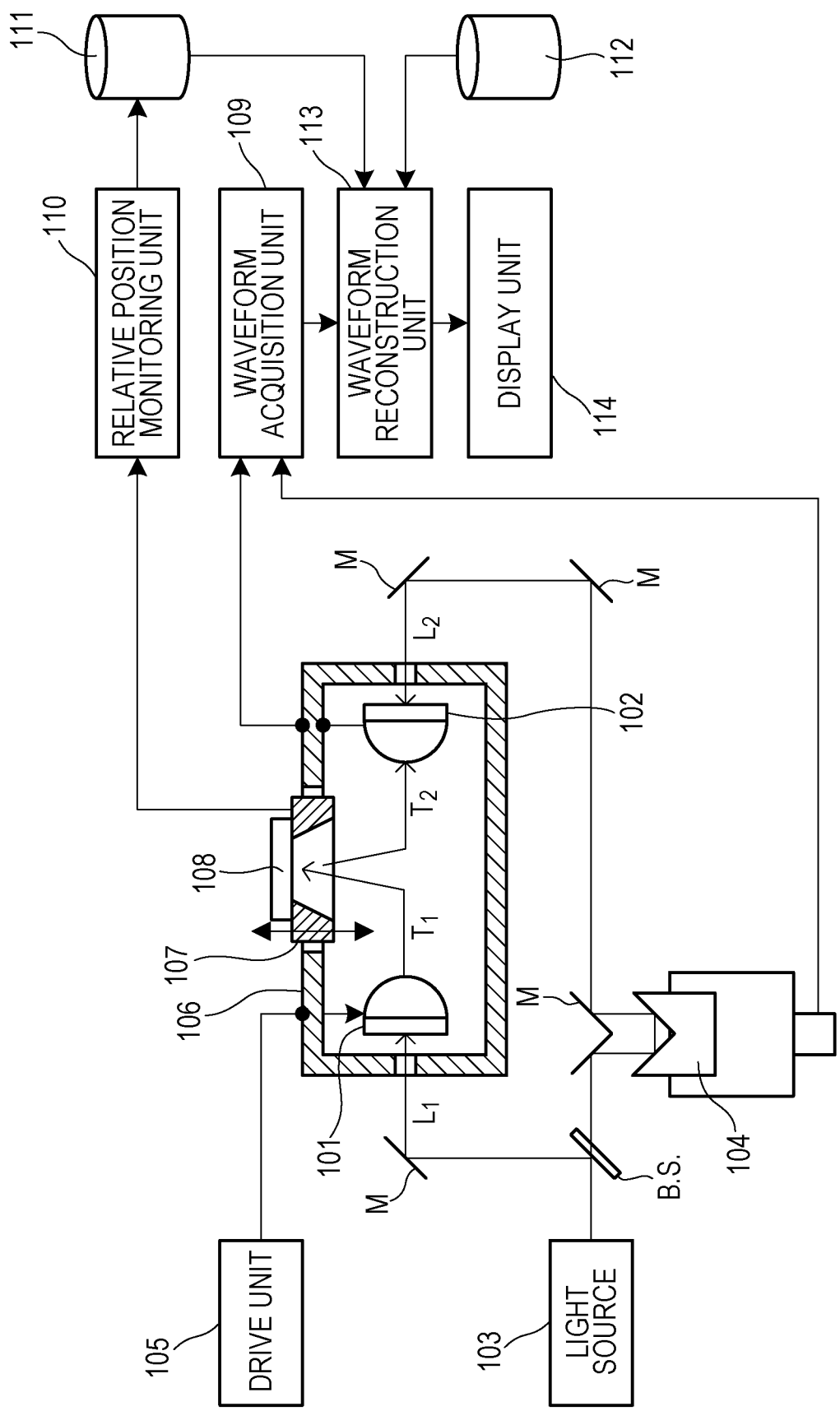

TRANSFAR MATRIX OF
$m^{th}$ LAYER: $A^{(m)}$

TRANSFAR MATRIX OF
$m^{th}$ INTERFACE: $B^{(m)}$

TRANSFAR MATRIX OF m LAYER(S):
$M = A^{(1)}B^{(1)}A^{(2)}B^{(2)} \cdots A^{(m)}B^{(m)} = \prod_{j=1}^{m} A^{(j)}B^{(j)}$ (OBJECT TO BE MEASURED)   (TOMOGRAPHY IMAGE)

APPARATUS FOR ACQUIRING INFORMATION FROM OBJECT TO BE MEASURED AND AQUIRING METHOD THEREFOR

BACKGROUND OF THE INVENTION

1. Field of the Invention

The present invention relates to an apparatus configured to acquire information on a physical property or a structure of an object to be measured by using a terahertz wave, and a method of acquiring information from an object to be measured using a terahertz wave. In particular, this application relates to an apparatus for measuring a terahertz wave in the time domain (THz-TDS apparatus or THz-Time Domain Spectroscopy apparatus).

2. Description of the Related Art

A terahertz wave is typically an electromagnetic wave having a frequency component of any frequency band in a range from 0.03 THz to 30 THz. In such a frequency band, there exists a large number of distinctive absorption derived from a structure and a state of various substances such as a biomolecule. Utilizing this feature, an examination technique for performing an analysis, identification, and the like of a substance in a nondestructive manner has been developed. Such a technique is expected to be applied to a safe imaging technology, which may take place or enhance conventional X-ray technology and high-speed communication. Specifically, application terahertz technology to a tomography apparatus that visualizes inside a substance is attracting attention. In a tomography apparatus, utilizing a transmittance feature of the terahertz wave, visualization of an inner structure at a depth of several 100 µm to several 10 mm is expected.

A large number of distinctive absorption related to atmospheric moisture exits in the electromagnetic wave in the terahertz region. Therefore, in order to decrease this influence of the atmosphere, there has been often used an apparatus configuration in which a part where the terahertz wave is propagated is isolated from the atmosphere, and in which an ambient atmosphere in the part where the terahertz wave is propagated is adjusted. International patent application publication WO03/058212 discloses, in order to measure various objects to be measured without changing a state of an adjusted ambient atmosphere, an apparatus configuration in which a measuring window, through which a terahertz wave is transmitted, is provided in a part of a casing used for isolation from the atmosphere, and the object to be measured is placed in chamber on that window.

As a technique in WO03/058212, in a configuration in which an object to be measured is placed on a measuring window provided in a part of a casing, which includes a reflection measuring system, a position of the object to be measured is fixed relative to a focal position of the terahertz wave. Therefore, in this configuration, an adjustment of a relative position between the focal position of the terahertz wave and the object to be measured is limited and difficult. For example, in an optical arrangement in FIG. 10B, which is also used for describing the present invention, the following phenomenon has been confirmed as a result of a study by the present inventor. Using FIG. 10B, a case where an optical distance is measured based on a time interval between terahertz wave pulses reflected from a first interface 1018 and a second interface 1019 of the object to be measured in is studied. Here, between a case where two interfaces are within a parallel propagation region 1022 and a case where any interface exists in a light collection process region 1021, an optical distance acquired by an apparatus changes. In other words, depending on a position of the object to be measured relative to a focal position of the terahertz wave, a measuring value of optical thickness of the object to be measured may change.

Here, the parallel propagation region 1022 is a region where the terahertz wave propagates in parallel with an optical axis of the terahertz wave, and this region wave-optically corresponds to a depth of focus. Herein, the parallel propagation region 1022 is also referred to as a focal position. Likewise, the light collection process region 1021 is defined as a region of a light-collecting process of the terahertz wave.

Taking this phenomenon into account, in an apparatus configuration in which the focal position of the terahertz wave is fixed relative to the position of the object to be measured, as is the case in WO03/058212, with regard to the object to be measured placed on an apparatus casing, it will be as follows. That is, when observing a surface or an inner structure of the object to be measured, a measurement value of an optical distance may change depending on a place, and an accurate observation of the structure of the object to be measured may become difficult. As a result, measuring reliability of an apparatus for acquiring an inner structure may decrease. Herein, the optical distance, which changes according to the focal position of the terahertz wave, is referred to as a secondary propagation distance.

SUMMARY OF THE INVENTION

An apparatus configured to acquire information on an object to be measured by irradiating the object with an electromagnetic wave pulse is disclosed. The apparatus includes: a generating unit configured to generate the electromagnetic wave pulse with which the object to be measured is irradiated; a detecting unit configured to detect the electromagnetic wave pulse from the object to be measured; a casing including at least a part of a propagation path of the electromagnetic wave pulse leading from the generating unit to the detecting unit; and a measuring window unit configured to change a propagation distance of the electromagnetic wave pulse by moving a measuring window disposed in a part of the casing. The object to be measured is disposed on an opposite side of the propagation path of the electromagnetic wave pulse inside the casing by interposing the measuring window.

Further features of the present invention will become apparent from the following description of exemplary embodiments with reference to the attached drawings.

BRIEF DESCRIPTION OF THE DRAWINGS

FIG. 1 is a schematic configuration view of an apparatus described in Embodiments 1 and 2 according to the present invention;

DESCRIPTION OF THE EMBODIMENTS

Figure 2A:
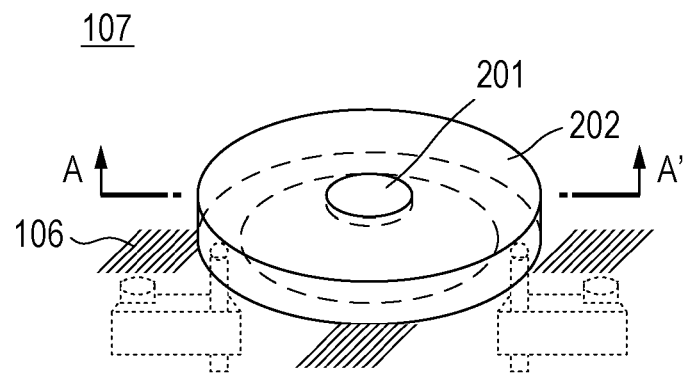
FIG. 2A is a perspective view illustrating a configuration of a measuring window unit.

An apparatus for acquiring a physical property or a structure of an object to be measured and a method thereof according to this embodiment are characterized in that a measuring window, which is fixed to a casing in a conventional apparatus, is configured to be movable. As a result, it is possible to adjust a focal position of an electromagnetic wave relative to a position of the object to be measured in an observation, whereby an accurate observation of the physical property or the structure of the object to be measured is made easier.

In this embodiment, the physical property or the structure of the object to be measured is observed by using an electromagnetic wave pulse reflected by the object to be measured. The electromagnetic wave pulse to be used may have a certain degree of transmittance relative to the object to be measured. Here, it is suitable to use a terahertz wave pulse in a case where a space between reflective portions of the object to be measured is from several 100 μm to several 10 mm in size, and where it is also desirable to obtain a physical property of the reflective portion and a region up to the reflective portion. The terahertz wave pulse has a component of any of the frequency band from 0.03 THz to 30 THz. Then, in this wavelength range, there exists a large number of distinctive absorption derived from a structure and a state of various substances such as a biomolecule. By using the transmittance and analyticity of the terahertz wave pulse, the apparatus and the method according to this embodiment are effective for acquiring not only information related to a structure of the object to be measured but also a physical property. Therefore, for example, information on whether or not a cell is an abnormal cell (cancer cell and the like) or not is also included in the "information on a physical property or a structure of the object to be measured" herein.

As described above, herein, a beam shape when the terahertz wave pulse is light collected is defined as below. That is, the beam shape of the terahertz wave pulse light concentrated by a light collection unit 1020 is considered separately for a light collection process region 1021 and a parallel propagation region 1022 as in FIG. 10B. The parallel propagation region 1022 is a region where the terahertz wave propagates in parallel, and this region wave-optically corresponds to a depth of focus. Herein, the parallel propagation region 1022 is also referred to as a focal position. Likewise, the light collection process region 1021 is defined as a region of a light-collecting process of the terahertz wave. Furthermore, a change in the propagation distance of the terahertz wave pulse accompanied by a change in a relative position between the focal position of the terahertz wave pulse and the object to be measured is simply referred to as a propagation distance change. In addition, as described above, a change in the optical propagation distance of the terahertz wave pulse caused by a shift of a measured region from the focal position of the terahertz wave pulse may also be referred to as a secondary propagation distance change. This embodiment is described based on such definitions of terms.

Embodiments of the present invention are described below in detail. Herein, a terahertz wave pulse is used as an electromagnetic wave pulse in descriptions.

(Embodiment 1)

Embodiments for carrying out an idea of the present invention are described with reference to the drawings. Using FIG. 1, a configuration of an apparatus for acquiring a physical property or a structure of an object to be measured according to this embodiment is described. This apparatus includes a generating unit 101, which generates a terahertz wave pulse T1, and a detecting unit 102, which detects a terahertz wave pulse T2 from an object to be measured 108, as units for handling the terahertz wave pulse.

A time waveform of the terahertz wave pulse $T_2$ is acquired by using the Time Domain Spectroscopy method. In order to acquire this time waveform, the apparatus includes at least the following configuration. The apparatus includes a light source 103 configured to output an excitation light used for generating and detecting the terahertz wave pulse. The apparatus includes a delay optical unit 104 configured to adjust an optical path length of an excitation light $L_2$ leading from the light source 103 to a detecting unit 102. The apparatus includes a waveform acquisition unit 109 configured to acquire the time waveform of the terahertz wave pulse $T_2$ by referring to a change in the optical path length of the excitation light $L_2$ defined by the delay optical unit 104 and an output from the detecting unit 102. Furthermore, the apparatus includes a drive unit 105 used for generating the terahertz wave pulse $T_1$ from the generating unit 101. The drive unit 105 is a voltage or a current source. In a case where a signal from the detecting unit 102 is detected by using a modulation and demodulation technique using a lock-in amplifier, the drive unit 105 may have a function to modulate the signal. The configuration of each unit of the apparatus described above may be any configuration as long as a time waveform of the terahertz wave pulse $T_2$ can be acquired in the end. For example, details of the configuration of each unit are described in Japanese Patent Application No. 2012-047462 by the present applicant. Note that in FIG. 1, M denotes a reflection mirror and B.S. denotes a beam splitter.

The apparatus according to this embodiment is different from a conventional apparatus in that it has the following configuration. In FIG. 1, the apparatus includes at least a part of a propagation path of the terahertz wave pulse leading from the generating unit 101, which generates the electromagnetic wave pulse irradiated on the object to be measured, to the detecting unit 102, and a casing 106, which enables an adjustment of an ambient atmosphere surrounding the propagation path. In a part of this casing 106, a measuring window unit 107 is movably provided. The measuring window unit 107 is within the propagation path of the terahertz wave pulse, and is a part that changes the propagation distance of the terahertz wave pulse. Specifically, the measuring window unit 107 is in a propagation path of the terahertz wave pulse and is a part including a configuration of a measuring window, which is movable for changing the propagation path of the terahertz wave pulse leading from the generating unit 101 to the detecting unit 102. The object to be measured 108 is disposed on an opposite side of the propagation path of the terahertz wave pulse inside the casing so as to sandwich the measuring window unit 107. By using such configuration, while keeping the ambient atmosphere inside the casing 106, the apparatus can adjust the position of the object to be measured 108 placed outside the casing 106 relative to the focal position of the terahertz wave. The measuring window may be detachably provided and may be prepared by a user.

Next, each unit is described in detail.

Figure 2B:
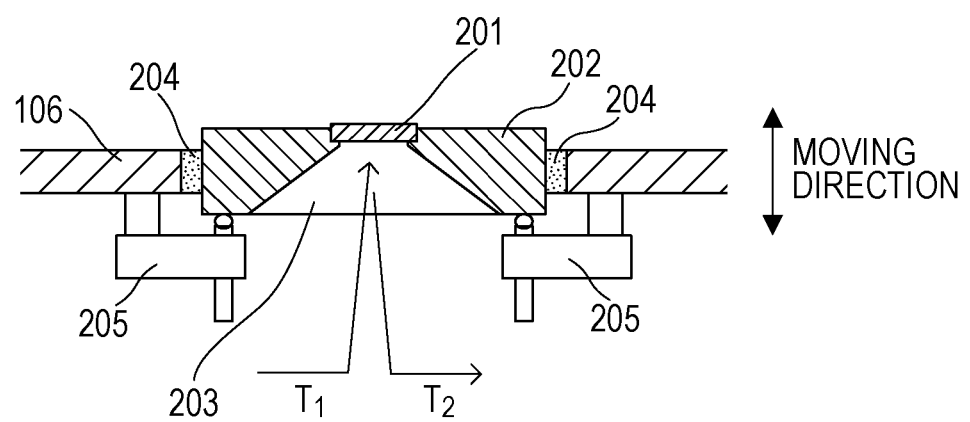
FIG. 2B is a sectional view illustrating a configuration of a measuring window unit, according to Embodiment 1.

FIGS. 2A and 2B are views illustrating one embodiment of the measuring window unit 107. FIG. 2A is a perspective view of the measuring window unit 107, and FIG. 2B is a sectional view of the measuring window unit 107 taken along line AA' illustrated in FIG. 2A. As illustrated in FIGS. 2A and 2B, the measuring window unit 107 is formed in a part of the casing 106. Then, the measuring window unit 107 includes a measuring window 201, a measuring window casing 202, a sealing part 204, and an actuator 205. The measuring window 201 supports the object to be measured 108 in the measuring window unit 107, and is a part where the terahertz wave pulse T1 enters the object to be measured 108. Furthermore, the measuring window 201 also plays a role of a cover for suppressing fluctuation of the ambient atmosphere adjusted by the casing 106. By the object to be measured 108 being in close contact with the measuring window 201, interfaces of the object to be measured 108 and the measuring window 201 are shaped along a shape of the measuring window 201. In other words, the shape of the object to be measured 108 can be re-shaped into a shape suitable for measuring. As a result, scattering and interference of the terahertz wave pulse derived from the shape of the object to be measured 108 can be suppressed, whereby a measuring accuracy can be improved.

Since the measuring window 201 is disposed in the propagation path of the terahertz wave pulse, it is preferred that a material having a superior transmittance to the terahertz wave pulse be used. For example, a resin such as polyethylene, Teflon (registered trademark), and cycloolefin polymer can be applied. A resin material in a porous form can be applied as well. Furthermore, a substrate material such as high resistor silicon, CVD (Chemical Vapor Deposition) diamond, and Z-cut quartz can also be applied. It is preferred that a flatness of the measuring window 201 be at a level such that the terahertz wave pulse is unable to recognize a structure thereof. Specifically, the flatness of about $\frac{1}{100}\lambda$ to $\frac{1}{20}\lambda$ is desirable relative to an effective wavelength $\lambda$ (typically, a center wavelength of a spectrum that the terahertz wave pulse has) of the terahertz wave pulse to be used. For example, in a case where $\lambda$ is 100 μm, it is preferred that the flatness of the measuring window 201 be from about one to five μm. Under such a condition, an influence of scattering from the measuring window 201 on the terahertz wave pulse can be suppressed. Furthermore, the flatness of the measuring window 201 also depends on a measuring resolution stored in a propagation distance database 111. For example, in a case where a change in the propagation distance of the terahertz wave pulse is measured for a relative position between the focal position of the terahertz wave pulse $T_1$ and the measuring window unit 107 in a 100-μm measuring performance, it is preferred that the flatness be a smaller value than this measuring performance. Furthermore, in a case where a measurement error is defined as an apparatus specification, it is preferred that the flatness be a smaller value than this measurement error.

Furthermore, it is preferred that the measuring window 201 have a clear interface in a part contacting the object to be measured 108. Therefore, a function may be added for adjusting a complex index of refraction $n_{com}$ (herein, the complex index of refraction is denoted by an n with a small tilde in the formula below, but in the descriptions, an n with a small tilde is simply denoted by $n_{com}$) of the measuring window 201 according to a physical property of the object to be measured 108. For example, an embodiment having a configuration in which all or a part of the measuring window 201 can be impregnated with liquid for adjusting an index of refraction may be considered. Specifically, a porous material including a granular or spongy structure of polypropylene, polysulfone, nylon, or polyethersulfone, which have high transmittance to the terahertz wave pulse $T_1$, can be applied as the measuring window 201. Then, as a material for the adjustment of the index of refraction, water, physiological saline, oil, ion water, formalin, phosphate buffer solution, alcohol, cell culture medium, sugar, hormone, protein, amino acid, and the like can be applied. It is preferred that these materials be transparent to the terahertz wave pulse to be used. Furthermore, these materials may be used alone or may be used by mixing a plurality of materials. In the descriptions above, the measuring window 201 is described separately from the object to be measured 108; however, the object to be measured 108 may also serve as the measuring window 201.

The measuring window casing 202 is a part for changing the propagation distance of the terahertz wave pulse by supporting the measuring window 201 and by moving the measuring window 201. In order to cause the terahertz wave pulse to reach the measuring window 201, an opening is provided in the measuring window casing 202, and the measuring window 201 is supported at the opening. As in FIG. 2B, in this embodiment, a recessed portion 203 is processed as the opening in the measuring window casing 202. This is to prevent a part of the terahertz wave pulse, which enters a part of the measuring window 201 and being reflected, from being blocked by the measuring window casing 202.

The measuring window casing 202 is disposed in the casing 106 through the actuator 205. In FIGS. 2A and 2B, the measuring window casing 202 moves in a normal line direction relative to a surface of the casing 106. FIGS. 2A and 2B illustrate an embodiment of the measuring window unit 107 to which an actuator 205, configured to be extensible by a motor, is applied. As a motor for the actuator 205, an actuator using a stepping motor, a linear motor, a piezo motor, or the like can be applied. A configuration using a non-rotational rod is preferred such that the measuring window casing 202 is not rotated in a moving direction by a rotating force of the rod being transmitted to the measuring window casing 202. In FIGS. 2A and 2B, two actuators 205 are used; however, the number thereof to be used is not limited to two.

Furthermore, these actuators 205 can be used as an inclination adjustment mechanism for adjusting an inclination of the measuring window 201 in the moving direction of the measuring window unit 107. Specifically, by using three actuators 205, the inclination of the measuring window casing 202 and the measuring window 201 can be adjusted for a pitch axis and a yaw axis in the moving direction. By this inclination adjustment mechanism, a reflection angle of the terahertz wave pulse $T_2$ from the measuring window unit 107 can be adjusted. Therefore, compared to an embodiment in which the measuring window unit 107 is fixed to the casing 106, an alignment of the terahertz wave can be made accurately, whereby a measuring accuracy of the apparatus is improved.

A reason why the measuring accuracy of the object to be measured is improved when the alignment of the terahertz wave is made accurately is described by using an example. This is from the patent application by the present applicant. A case in which a physical property of the object to be measured having at least a first reflective portion and a second reflective portion is acquired by irradiating the object to be measured with an electromagnetic wave pulse by the time domain spectroscopy method is considered. At a position where a first pulse is acquired by a waveform acquisition unit, a time waveform is acquired including at least the first pulse and a second pulse by the time domain spectroscopy method, by adjusting a difference in an optical path length by a time difference conversion in a delay unit. Furthermore, an adjustment amount of the measuring window monitored by a relative position monitoring unit and the acquired time waveform are stored. Then, a light collecting position of the electromagnetic wave pulse relative to the object to be measured is slightly moved. In this way, a position in which a parallel propagation region, which is a light collecting position of the electromagnetic wave pulse, overlaps with the first reflective portion of the object to be measured is calculated from a change in the stored adjustment amount and the time waveform, and the light collecting position of the electromagnetic wave pulse is moved to the first reflective portion of the object to be measured. The first pulse is acquired from a time waveform when the parallel propagation region, which is the light collecting position of the electromagnetic wave pulse, overlaps with the first reflective portion of the object to be measured, and an adjustment amount $Z_1$ of the measuring window necessary for moving the light collecting position and an optical path length difference $D_1$ at a position for acquiring the first pulse by the delay unit are acquired. Next, a light collecting position of the electromagnetic wave pulse is moved to the second reflective portion of the object to be measured, and the second pulse is acquired from a time waveform when the parallel propagation region, which is the light collecting position of the electromagnetic wave pulse, overlaps with the second reflective portion of the object to be measured. Then, an adjustment amount $Z_2$ of the measuring window unit necessary for moving the light collecting position and an optical path length difference $D_2$ at a position for acquiring the second pulse by the delay unit are acquired. Subsequently, based on an amount of change $|Z_2-Z_1|$ of the adjustment amount and an amount of change $|D_2-D_1|$ of the optical path length difference, the thickness and the index of refraction are calculated for a region sandwiched by the first reflective portion and the second reflective portion of the object to be measured. In this way, a position of each reflective portion can be accurately specified even in a case where a size of the region sandwiched by each reflective portion of the object to be measured is close to a size of the parallel propagation region of the electromagnetic wave pulse, whereby a detection accuracy of the thickness and the index of refraction of the region sandwiched by the first reflective portion and the second reflective portion can be improved. When the terahertz wave pulse is used as the electromagnetic wave pulse, by using the transmittance of the terahertz wave pulse, it is possible to visualize an inner structure or to specify a physical property at a depth of about several 100 µm to several 10 mm.

Going back to descriptions of FIGS. 2A and 2B, the sealing part 204 is disposed in a space between the casing 106 and the measuring window casing 202. The sealing part 204 is used for suppressing fluctuation of an ambient atmosphere adjusted in the casing 106. The sealing part 204 is provided in a part where the casing 106 and the measuring window casing 202 come in contact, whereby a low-friction material such as fluororesin, nitrile rubber, silicon rubber, and a high molecule weight polyethylene is preferred. Furthermore, a metal or a resin containing lubricant can also be applied.

Figure 3A:
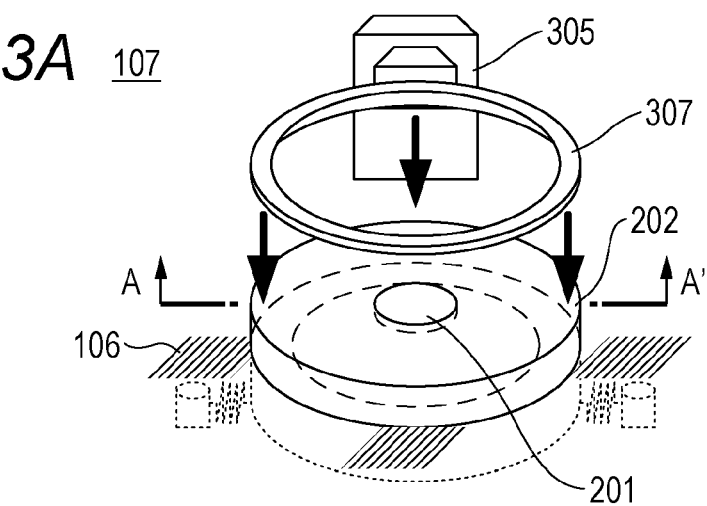
FIGS. 3A to 3C are views illustrating the measuring window unit according to a modification of Embodiment 1.
Figure 3B:
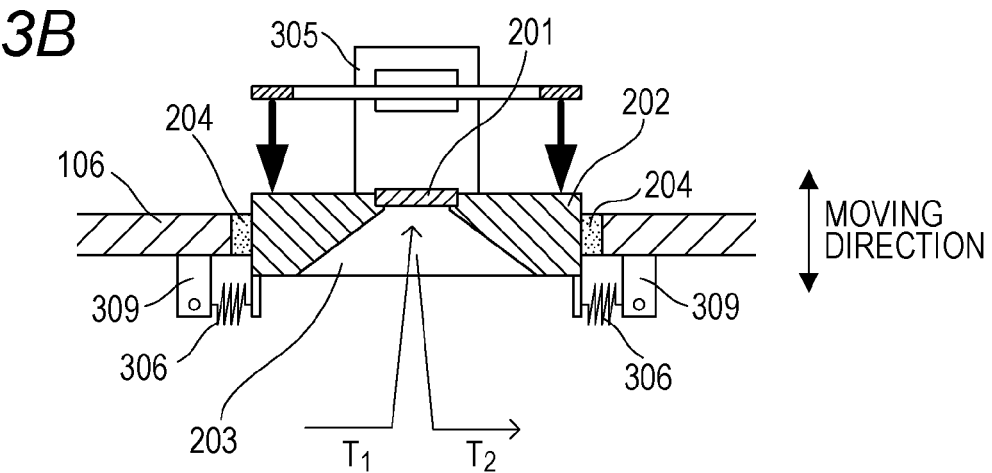
Figure 3C:
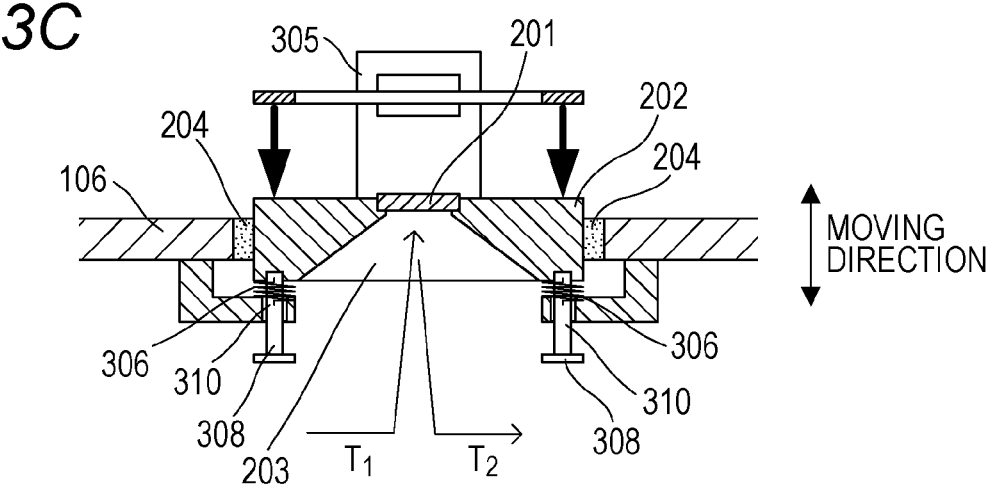

FIGS. 3A to 3C are views illustrating a modification of the measuring window unit 107. In FIGS. 3A to 3C, a difference from the measuring window unit 107 illustrated in FIGS. 2A and 2B is a disposition of an actuator used for moving the measuring window casing 202. Specifically, the actuator 205 in FIG. 2B is disposed inside the casing 106 and is fixed to the casing 106, while an actuator 305 in FIGS. 3A to 3C is disposed outside the casing 106. The actuator 305 has a pressing member 307. The actuator 305, by pressing the pressing member 307 to the measuring window casing 202, transmits a force from the actuator 305 to the measuring window casing 202. As a result, the measuring window casing 202 is moved. FIG. 3B is a sectional view taken along line AA' of FIG. 3A. As illustrated in the drawing, the measuring window unit 107 has an extensible part 306. One end of the extensible part 306 is connected to a fixed part 309 provided in the casing 106. For example, a tensile coil spring can be applied as the extensible part 306. The measuring window casing 202 is disposed in the casing 106 through an extensible part 306 by a pulling force of the extensible part 306. More specifically, the measuring window casing 202 is moved and disposed in any position by a balance between a force applied from the actuator 305 and the force of the extensible part 306 to lift up the measuring window casing 202.

FIG. 3C is a modification of FIG. 3B. Specifically, in FIG. 3C, there is a difference in a configuration where the measuring window casing 202 is disposed in the casing 106. As in FIG. 3C, the measuring window casing 202 is fixed to the casing 106 by the extensible part 306 and a guide screw 308. Specifically, the guide screw 308 is movable in a depth direction of a guide hole 310 provided in the casing 106, and the measuring window casing 202 is fixed to the casing 106 by the force of the extensible part 306. For example, a compression coil screw or a disk spring can be applied as the extensible part 306. The extensible part 306 is disposed between the measuring window casing 202 and the guide hole 310, and the guide screw 308 is inserted into a center of the extensible part 306.

In general, an actuator having a motor tends to have a large configuration; however, in the configuration in FIGS. 3A to 3C, it is possible to dispose this actuator outside the casing 106. Therefore, an area occupied by parts disposed inside the casing 106 can be decreased, whereby a volume inside the casing 106 can be decreased. As a result, the time necessary for adjusting the ambient atmosphere inside the casing 106 can be reduced, and miniaturization of the apparatus becomes easier. Furthermore, by using the extensible part 306 in the measuring window unit 107, it is possible to absorb a vibration from outside. When an unnecessary vibration occurs, a position of the measuring window unit 107 changes, whereby the propagation distance of the terahertz wave pulse fluctuates, and the measuring accuracy may decrease when acquiring a time waveform of the terahertz wave pulse. By absorbing this unnecessary vibration, it is possible to stabilize the measuring accuracy of the apparatus.

In the configuration of the measuring window unit 107 in FIGS. 2A and 2B, the actuator 205, which supports the measuring window casing 202, is used as the inclination adjustment mechanism. In contrast, in the configuration of the measuring window unit 107 in FIGS. 3A to 3C, the actuator 305 provided outside the casing 106 is used as the inclination adjustment mechanism. Specifically, the actuator 305 has a mechanism to adjust an inclination of the pressing member 307, and by pressing the pressing member 307 against the measuring window casing 202 while keeping the inclination of the pressing member 307, it is possible to adjust the reflection angle of the terahertz wave pulse $T_2$.

Figure 12A:
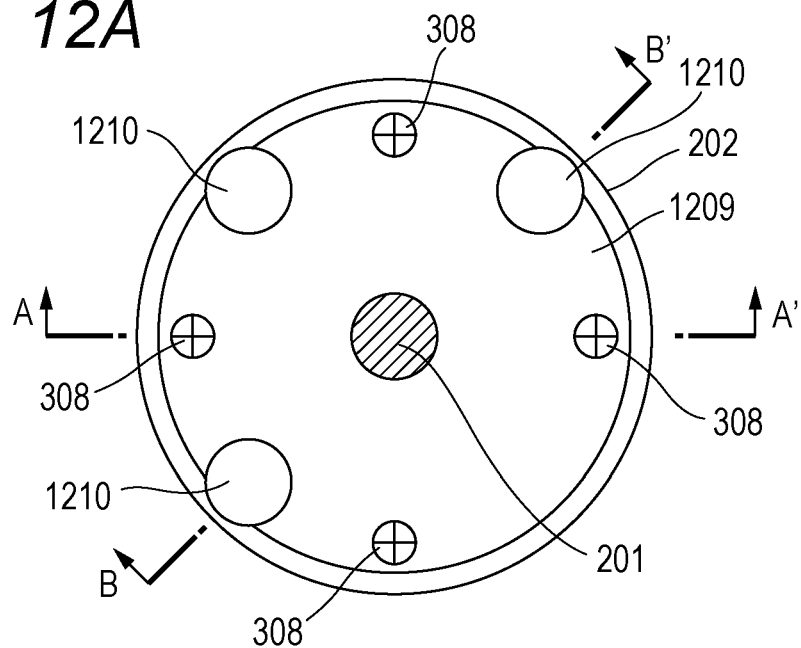
FIGS. 12A to 12C are views illustrating a modification of a measuring window unit according to Embodiment 1.
Figure 12B:
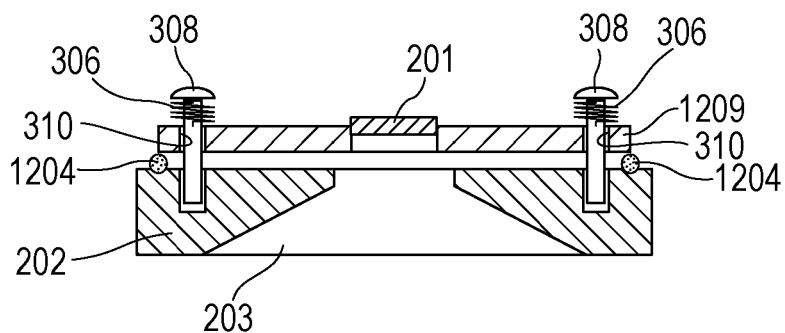
Figure 12C:
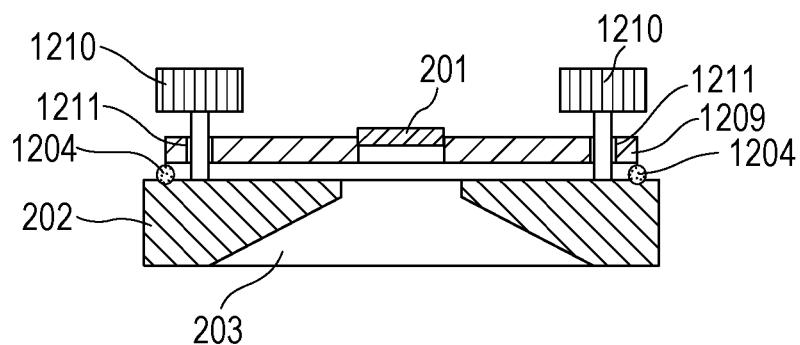

In the configurations in FIGS. 2A and 2B, and in FIGS. 3A to 3C, as the inclination adjustment mechanism for adjusting the inclination of the measuring window 201 relative to the moving direction of the measuring window unit 107, the actuators 205 and 305 used for moving the measuring window casing 202 are used. However, the measuring window unit 107 may have this inclination adjustment mechanism separately. For example, FIGS. 12A to 12C is an exemplary embodiment in which the inclination adjustment mechanism is provided separately in the measuring window unit 107. Note that in the measuring window unit 107 in FIGS. 12A to 12C, a configuration necessary for moving the measuring window casing 202 is omitted, but practically, an above-described mechanism necessary for moving the measuring window unit 107 can be applied.

FIG. 12A is a top view of the measuring window unit 107, FIG. 12A is a sectional view of the measuring window unit 107 taken along line AA' of FIG. 12A, and FIG. 12C is a sectional view of the measuring window unit 107 taken along line BB' of FIG. 12A. A difference from the measuring window unit 107 described above is an inclination adjustment plate 1209 for adjusting an inclination of the measuring window 201. Specifically, as in FIG. 12B, the inclination adjustment plate 1209 is fixed to the measuring window casing 202 by the guide screw 308. The inclination adjustment plate 1209 has a guide hole 310, and the guide screw 308 moves in a depth direction of the guide hole 310. The extensible part 306 is disposed between the inclination adjustment plate 1209 and an edge of the guide screw 308. The guide screw 308 is inserted into the center of the extensible part 306, and the inclination adjustment plate 1209 is pressed against the measuring window casing 202 by the force of the extensible part 306. A compression spring or a disk spring can be applied as the extensible part 306. A sealing part 1204 is inserted between the inclination adjustment plate 1209 and the measuring window casing 202 to suppress the ambient atmosphere adjusted in the casing 106 from being fluctuated. An O ring can be applied as the sealing part 1204. Since the sealing part 1204 is deformed by a force applied from the inclination adjustment plate 1209, a material having a small hardness is preferred as a material used in the sealing part 1204. As a result, the sealing part 1204 is deformed along an inclination of the inclination adjustment plate 1209, whereby a sealed state is maintained, and fluctuation of the ambient atmosphere becomes small.

Furthermore, as in FIG. 12C, the inclination adjustment plate 1209 has a screw bush 1211 and an adjusting screw 1210. An edge of the adjusting screw 1210 abuts onto the measuring window casing 202. A distance between the measuring window casing 202 and the inclination adjustment plate 1209 is adjusted by a push-in amount of the adjusting screw 1210. In a configuration of the measuring window unit 107 in FIG. 12A, three adjusting screws 1210 are used, and the inclination of the measuring window 201 can be adjusted for a pitch axis and a yaw axis in a moving direction. By this inclination adjustment mechanism, a reflection angle of the terahertz wave pulse from the measuring window unit 107 can be adjusted. Therefore, compared to an embodiment in which the measuring window unit 107 is fixed to the casing 106, an alignment of the terahertz wave can be made accurately, whereby a measuring accuracy of the apparatus is improved.

With regard to the apparatus according to this embodiment, the apparatus has the measuring window unit 107, which is movable relative to the casing 106 for adjusting the ambient atmosphere, an adjustment between the focal position of the terahertz wave and the position of the object to be measured 108 becomes possible in a state in which the fluctuation of the adjusted ambient atmosphere is suppressed. As a result, since a measurement can be made in a parallel propagation region 1022 where the terahertz wave pulse propagates in parallel (see FIG. 10B), an accurate observation of a surface or an inner structure of the object to be measured becomes possible, whereby the reliability of the apparatus is improved.

(Embodiment 2)

As a method of acquiring a physical property of an object to be measured 108, there is a method of reconfiguring a response of a terahertz wave pulse by calculation using a transfer matrix (see, for example, Proceedings of SPIE, Vol. 5692, 241-254 (2005)). In an information acquiring apparatus of the object to be measured according to this embodiment, the apparatus according to Embodiment 1 is applied to an apparatus for acquiring a physical property of the object to be measured 108 by using a transfer matrix. Note that a description is omitted for any part common with the descriptions above.

The apparatus according to this embodiment is described by using FIG. 1. To a configuration of the apparatus according to Embodiment 1, the apparatus according to this embodiment is added with the following configuration. A relative position monitoring unit 110 is a part for monitoring a relative position between a focal position of a terahertz wave pulse $T_1$ and a measuring window unit 107. A propagation distance database 111 is a part for outputting information used in a calculation of a change dL of a secondary propagation distance of the terahertz wave pulse, relative to the relative position, caused by a change in an optical system arrangement existing in the propagation path of the terahertz wave pulse. More specifically, an influence of an arrangement relationship between the measuring window 201, which constitutes the measuring window unit 107, and the focal position of the terahertz wave pulse $T_1$ on the propagation distance of the terahertz wave pulse is stored.

Figure 10A:
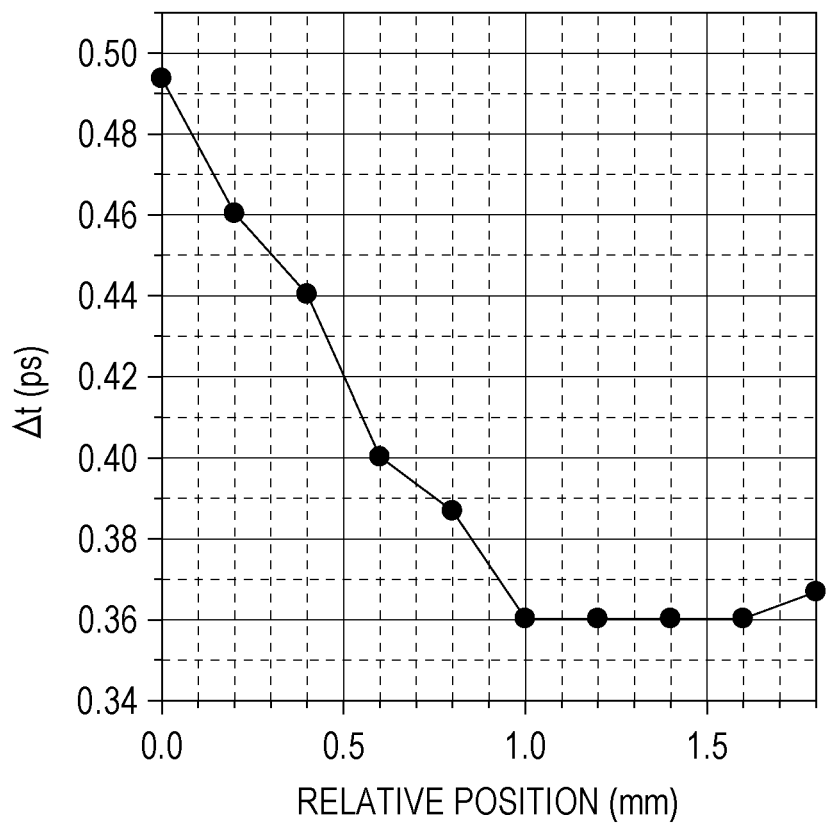
FIG. 10A illustrates data stored in a propagation distance database.
Figure 10B:
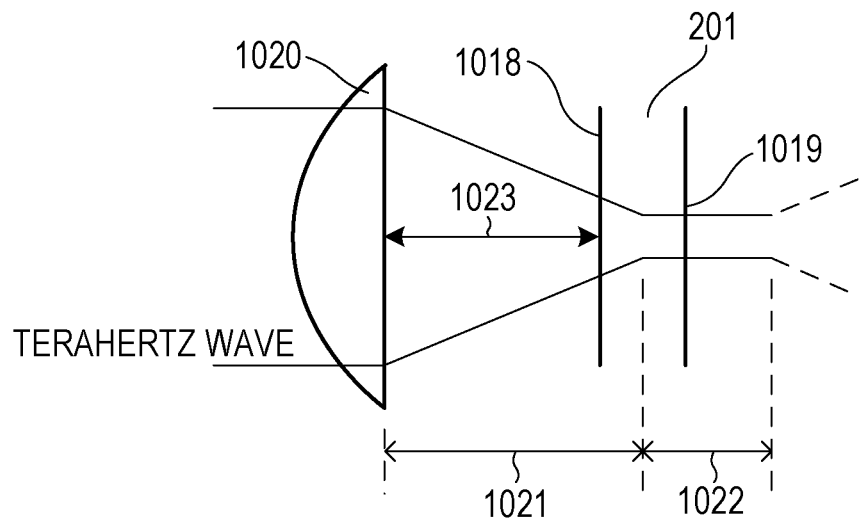
FIG. 10B illustrates a problem in the prior art.

FIG. 10A is a view illustrating an exemplary data stored in the propagation distance database 111. FIG. 10B is a view for describing the data stored in the propagation distance database 111. In FIG. 10B, the measuring window 201 has interfaces, each having a varying index of refraction on a boundary with outside. Herein, these are referred to as a first interface 1018 and a second interface 1019. The terahertz wave pulse is light-collected on the measuring window 201 by a light collection unit 1020. At this time, a space between the light collection unit 1020 and the measuring window 201 is defined as a relative position 1023. By measuring a time waveform of the terahertz wave pulse reflected from the measuring window 201, a reflection wave from the first interface 1018 and the second interface 1019 can be observed. A time interval Δt of this reflection wave is a value reflecting an optical distance of the measuring window 201 in FIG. 10B. An observed optical distance (secondary propagation distance) of the measuring window 201 changes according to the arrangement relationship between the focal position of the terahertz wave pulse and the measuring window 201.

FIG. 10A is a graph in which the time interval Δt of the terahertz wave pulse reflected from the measuring window 201 is plotted when the relative position 1023 is changed. In the propagation distance database 111, such information is stored for each material to be used. In a graph in FIG. 10A, information when a 30 μm-thick porous film is used as the measuring window 201 is plotted. The time interval Δt of the terahertz wave pulse described in the graph can be converted into the propagation distance of the terahertz wave pulse by using a light speed c and a physical property value of the measuring window 201. Here, as in FIG. 10B, a state in which the first interface 1018 of the measuring window 201 is in the light collection process region 1021, and the second interface 1019 is in the parallel propagation region 1022, corresponding to the focal position is defined as 0 mm as an initial position of the measuring window 201. This position is defined by a measurer. For example, the initial position is converted into 0 mm as a standard; however, it is also possible to plot actually measured values of the relative position 1023 without performing any conversion. According to the graph in FIG. 10A, it is confirmed that as the relative position 1023 becomes larger, the time interval Δt of the terahertz wave pulse becomes smaller, and when the relative position 1023 exceeds 1 mm, the time interval Δt indicates almost a constant value. Then, a trend has been confirmed that the time interval Δt becomes larger again when the relative position 1023 exceeds 1.6 mm. As a result, for example, the parallel propagation region 1022 corresponding to the focal position can be defined to be from 1.0 mm to 1.6 mm for the relative position 1023. In other words, it is apparent in the exemplary case described herein that the parallel propagation region 1022 corresponding to the focal position has a region of about 0.6 mm inside the measuring window 201. In a case where the physical property of the measuring window 201 is already-known, it is also possible to convert it into a region in a free space. In this way, even for a substance having the same shape, an optical propagation distance of the terahertz wave pulse changes according to a relationship between the focal position of the terahertz wave pulse and an arrangement position of the object to be measured. Specifically, in a case where the object to be measured is on the focal position of the terahertz wave pulse, the optical propagation distance of the terahertz wave pulse depends on the physical property of the object to be measured. However, in a case where the object to be measured is not on the focal position of the terahertz wave pulse, a change derived from the optical system (corresponding to a secondary propagation distance) is added the optical propagation distance of the terahertz wave pulse in addition to the physical property of the object to be measured. That is, it is apparent that the secondary propagation distance of the terahertz wave pulse changes according to an arrangement position between the focal position of the terahertz wave pulse and the object to be measured.

Note, however, that the data stored in the propagation distance database 111 described herein, is the data of certain thickness; however, it may also be data in the following format in order to enhance a universal use. For example, from actually measured data related to a material in multiple thicknesses, it is possible to calculate a change in a time interval of a reflected terahertz wave pulse to a change in the material thickness, or to calculate a trend in a change of a size of the parallel propagation region 1022 sensed by the material. By using the propagation distance database 111, it is possible to increase a range in which the propagation distance database 111 can be applied, whereby a universal use of the apparatus and the method is increased.

Furthermore, with regard to the time waveform of the terahertz wave pulse acquired by a waveform acquisition unit 109, a positional change of a peak-to-peak value of the time waveform of the terahertz wave pulse accompanied by moving of a reflecting interface existing in the atmosphere (free space) may also be stored in the propagation distance database 111. By using this data, for example, it is possible to calculate the time interval Δt of the terahertz wave pulse at a certain relative position 1023 by obtaining a difference in the position of the peak-to-peak values of two reflecting interfaces. Then, in a state where this gap between reflecting interfaces is maintained, by selecting data to use such that the relative position 1023 changes and by performing a similar calculation successively, it is possible to acquire a graph approximated to FIG. 10A. In this graph, a complex index of refraction $n_{com}$ is one, and for a material having a thickness defined by the measurer, it is equivalent to plotting a change in the propagation distance relative to a change in the focal position of the terahertz wave pulse. Using this data, by multiplying any complex index of refraction $n_{com}$, the propagation distance database 111 can output a change in a secondary propagation distance of the terahertz wave pulse related to a material having any thickness and a complex index of refraction $n_{com}$. By using the propagation distance database 111, it is possible to increase a range in which the propagation distance database 111 can be applied, whereby a universal use of the apparatus and the method is increased.

In a case where measuring of the object to be measured 108 placed on the measuring window 201 is performed, if a part to observe of the object to be measured 108 is on the focal position, a measuring accuracy of an optical distance can be maintained since the terahertz wave pulse can be regarded as a parallel beam. However, in a case where a part to observe of the object to be measured 108 partially exists in a light collection process region 1021, a secondary propagation distance of the terahertz wave pulse changes. As already described, this change in the secondary propagation distance is defined as a change derived from an optical system and not from a physical property of the object to be measured, and is expressed as a change dL in the secondary propagation distance of the terahertz wave pulse. It is preferred that the change dL in the secondary propagation distance of the terahertz wave pulse be dealt with as it may cause a measurement error depending on a measuring condition. In a method according to the present invention described below includes a method of suppressing this error.

Going back to the description of FIG. 1, a physical property database 112 is a part where an identification name of a substance and information on the physical property of the substance are stored. The stored physical property includes, for example, a complex index of refraction $n_{com}$, an absorption coefficient α, a transmittance, and a reflectance. It is preferred that a frequency distribution of physical property in the frequency domain to measure be stored.

The waveform acquisition unit 109 is the same as that in the above-described Embodiment 1. The waveform acquisition unit 109 outputs a measurement waveform $E_{meas}(t)$ from the object to be measured 108. A waveform reconstruction unit 113 is a part for structuring a reconstructed waveform $E_{rec}(t)$ by using the change dL in the propagation distance of the terahertz wave pulse obtained from the propagation distance database 111 and the physical property information stored in the physical property database 112. Specifically, a perfect reflection waveform of the terahertz wave from the measuring window unit 107 is referred to as a reference waveform $E_{ref}(t)$. By using this reference waveform $E_{ref}(t)$ and information from the propagation distance database 111 and the physical property database 112, the reconstructed waveform $E_{rec}(t)$ approximated to the measurement waveform $E_{meas}(t)$ is calculated and structured. This calculation expresses a propagation of an electromagnetic wave as a transfer matrix, and calculates the reconstructed waveform $E_{rec}(t)$ through optimization of the transfer matrix. By using a variable value of the transfer matrix obtained through the optimization of the reconstructed waveform $E_{rec}(t)$, a physical property of the object to be measured 108 is acquired.

Figure 9A:
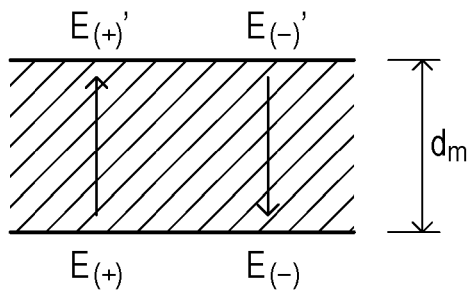
FIGS. 9A to 9C are views for describing a transfer matrix used in a waveform reconstructing unit.
Figure 9B:
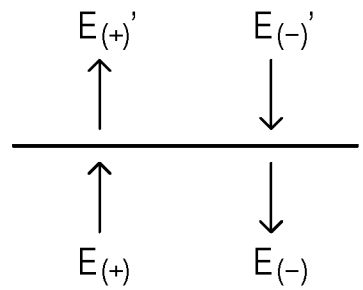
Figure 9C:
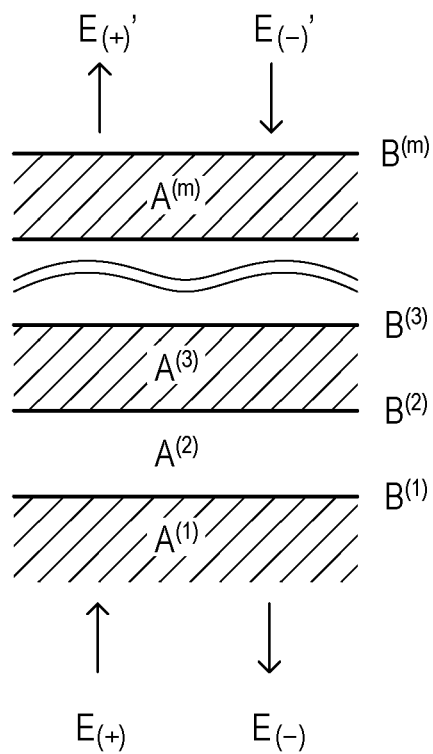

An operation of the waveform reconstruction unit 113 is described with reference to the drawings. FIGS. 9A to 9C are views illustrating the transfer matrix used in the waveform reconstruction unit 113. FIG. 9A is a view illustrating the transfer matrix for a layer of an object. FIG. 9B is a view illustrating the transfer matrix for an interface between objects. FIG. 9C is view illustrating the transfer matrix in an embodiment including a plurality of layers and interfaces. Here, the transfer matrix for the $m^{th}$ layer is denoted by $A^{(m)}$, and a transfer matrix for the $m^{th}$ interface is denoted by $B^{(m)}$. Then, the transfer matrix for a layer m is denoted by M. Furthermore, in the drawing, $E_{(+)}$ indicates a progressive wave, and $E_{(-)}$ indicates a regressive wave. In describing a transfer matrix M used in the waveform reconstruction unit 113, the complex index of refraction $n_{com}$ and the absorption factor α of the object is defined as below.

[Formulas 1 and 2]

$$\tilde{n} = n - ik \quad (1)$$

$$\alpha = \frac{4\pi\nu\kappa}{c} \quad (2)$$

Here, n represents an index of refraction, κ represents an extinction coefficient, c represents a light speed, ν represents a frequency, and k represents a wave. Furthermore, the wave number k is expressed in the following formula (3).

[Formula 3]

$$k = \frac{2\pi\nu\tilde{n}}{c} \quad (3)$$

At this time, the progressive wave $E_{(+)}$ and the regressive wave $E_{(-)}$ are defined in the following formula.

[Formula 4]

$$E_{(\pm)}(\nu) = |E_{(\pm)}(\nu)|\exp[i(2\pi\nu t \pm kx)] \quad (4)$$

Here, t represents the time, and x represents a position vector.

By using FIGS. 9A to 9C, the transfer matrix used in this embodiment is described. It is assumed that the object to be measured has a plurality of layers. In FIG. 9A is a view illustrating the transfer matrix for the $m^{th}$ layer of the object to be measured, and the thickness of the $m^{th}$ layer is denoted by $d_m$. Then, the index of refraction, the wave number, and the absorption factor of the $m^{th}$ layer are expressed as $n_{com-m}$, $k_m$, and $\alpha_m$. $E_{(+)}'$ and $E_{(-)}'$ are the progressive wave and the regressive wave that have propagated the layer. In FIG. 9A, when a direction in which the electromagnetic wave propagates from $E_{(+)}(\nu)$ to $E_{(+)}'(\nu)$ is used as a standard, $E_{(+)}'$ and $E_{(-)}'$ are represented by the following formulas.

[Formulas 5 and 6]

$$E_{(+)}'(\nu) = E_{(+)}(\nu)\exp[-ik_m d_m] \quad (5)$$

$$E_{(-)}'(\nu) = E_{(-)}(\nu)\exp[ik_m d_m] \quad (6)$$

At this time, in FIG. 9A, when the transfer matrix of the $m^{th}$ layer is $A^{(m)}$, from formulas (5) and (6), $A^{(m)}$ is represented by the following formula.

[Formula 7]

$$\begin{pmatrix} E_{(+)}(\nu) \\ E_{(-)}(\nu) \end{pmatrix} = A^{(m)} \begin{pmatrix} E_{(+)}'(\nu) \\ E_{(-)}'(\nu) \end{pmatrix} \quad (7)$$

$$= \begin{pmatrix} \exp[ik_m d_m] & 0 \\ 0 & \exp[-ik_m d_m] \end{pmatrix} \begin{pmatrix} E_{(+)}'(\nu) \\ E_{(-)}'(\nu) \end{pmatrix}$$

As it is apparent from formula (7), the transfer matrix $A^{(m)}$ represents attenuation and a phase change of the electromagnetic wave when it propagates the layer. FIG. 9B is a view illustrating the transfer matrix of the $m^{th}$ interface of the object to be measured. Specifically, an interface between the layer m and a layer m+1 is referred to as an $m^{th}$ boundary. In the figure, the transfer matrix of the $m^{th}$ interface is denoted by $B^{(m)}$. At this time, in a case where the electromagnetic wave propagates in a direction from the layer m to the layer m+1, a complex amplitude transmittance $t_{m, m+1}$ and a complex amplitude reflectance $r_{m, m+1}$ at the $m^{th}$ boundary is represented by the following formulas.

[Formula 8]

$$t_{m,m+1} = \frac{2\tilde{n}_m}{\tilde{n}_{m+1} + \tilde{n}_m} \quad (8)$$

[Formula 9]

$$r_{m,m+1} = \frac{\tilde{n}_{m+1} - \tilde{n}_m}{\tilde{n}_{m+1} - \tilde{n}_m} \quad (9)$$

At this time, a relationship among $E_{(+)}$, $E_{(-)}$, $E_{(+)}'$, and $E_{(-)}'$ in FIG. 9B is represented by the following formulas.

[Formulas 10 and 11]

$$E_{(+)}'(\nu) = t_{m,m+1} E_{(+)}(\nu) + r_{m+1,m} E_{(-)}'(\nu) \quad (10)$$

$$E_{(-)}(\nu) = r_{m,m+1} E_{(+)}(\nu) + t_{m+1,m} E_{(-)}'(\nu) \quad (11)$$

Furthermore, when a transfer matrix of the $m^{th}$ interface in FIG. 9B is denoted by $B^{(m)}$, from formulas (10) and (11), $B^{(m)}$ is represented by the following formula.

[Formula 12]

$$\begin{pmatrix} E_{(+)}(\nu) \\ E_{(-)}(\nu) \end{pmatrix} = B^{(m)} \begin{pmatrix} E_{(+)}'(\nu) \\ E_{(-)}'(\nu) \end{pmatrix} \quad (12)$$

$$= \begin{pmatrix} \dfrac{1}{t_{m,m+1}} & -\dfrac{r_{m+1,m}}{t_{m,m+1}} \\ \dfrac{r_{m,m+1}}{t_{m,m+1}} & t_{m+1,m} - \dfrac{r_{m,m+1} r_{m+1,m}}{t_{m,m+1}} \end{pmatrix} \begin{pmatrix} E_{(+)}'(\nu) \\ E_{(-)}'(\nu) \end{pmatrix}$$

Formula (12) can be deformed as follows by using formulas (8) and (9).

[Formula 13]

$$\begin{pmatrix} E_{(+)}(\nu) \\ E_{(-)}(\nu) \end{pmatrix} = B^{(m)} \begin{pmatrix} E_{(+)}'(\nu) \\ E_{(-)}'(\nu) \end{pmatrix} \quad (13)$$

$$= \frac{1}{2\tilde{n}_m} \begin{pmatrix} \tilde{n}_{m+1} + \tilde{n}_m & \tilde{n}_{m+1} - \tilde{n}_m \\ \tilde{n}_{m+1} - \tilde{n}_m & \tilde{n}_{m+1} + \tilde{n}_m \end{pmatrix} \begin{pmatrix} E_{(+)}'(\nu) \\ E_{(-)}'(\nu) \end{pmatrix}$$

As in formula (13), the transfer matrix $B^{(m)}$ of the $m^{th}$ interface can be expressed simply by a complex index of refraction of a material contacting through the interface. As in FIG. 9C, in a case where the transfer matrix is M when the object to be measured includes a plurality of layers, the transfer matrix M is represented by a product of the transfer matrix of each layer and each interface.

[Formula 14]

$$M = A^{(1)} B^{(1)} A^{(2)} B^{(2)} A^{(3)} B^{(3)} \ldots A^{(m)} B^{(m)} = \Pi_{j=1}^{m} A^{(j)} B^{(j)} \quad (14)$$

As a result, the progressive wave $E_{(+)}$ and the regressive wave $E_{(-)}$ can be represented by as follows by using the transfer matrix M.

[Formula 15]

$$\begin{pmatrix} E_{(+)}(v) \\ E_{(-)}(v) \end{pmatrix} = M \begin{pmatrix} E'_{(+)}(v) \\ E'_{(-)}(v) \end{pmatrix} \tag{15}$$

As described above, the waveform reconstruction unit 113 uses the perfect reflection waveform of the terahertz wave from the measuring window unit 107 as the reference waveform $E_{ref}(t)$, and calculates the reconstructed waveform $E_{rec}(t)$, which is approximated to the measurement waveform $E_{meas}(t)$ by using the reference waveform $E_{ref}(t)$. In a case where the apparatus configuration is such that the reflected terahertz wave pulse from the object to be measured 108 illustrated in FIG. 1 is measured, the progressive wave $E_{(+)}$ is information in a frequency domain of the reference waveform $E_{ref}(t)$. Likewise, the regressive wave $E_{(-)}$ is information in a frequency domain of the reconstructed waveform $E_{rec}(t)$. In this embodiment, the information in the frequency domain of the regressive wave $E_{(-)}$ is converted into time domain information, which is compared with the measurement waveform $E_{meas}(t)$, and optimization of the transfer matrix M is performed. Specifically, the complex index of refraction and the thickness of each layer is optimized. In performing an optimization of the transfer matrix, in a case where a part of a surface or an inner structure of the object to be measured 108 is already-known, this already-known information may be acquired by referring to the physical property database 112. Furthermore, for the information on a surface or an inner structure of the object to be measured 108, in a case where there is a candidate, a range of a parameter to be optimized may be limited by referring to physical property information of the candidate.

As described above, the secondary propagation distance of the terahertz wave pulse changes depending on the relationship between the focal position of the terahertz wave pulse and the arrangement positions of the object to be measured. For example, in FIG. 9C, even in a case where a physical property is the same for a part corresponding to a transfer matrix $A^{(1)}$ and a part corresponding to the propagation distance of the terahertz wave pulse changes depending on a focal position of the terahertz wave pulse. For example, a case in which a focus of the terahertz wave pulse exists in a part corresponding to the transfer matrix $A^{(1)}$, and a part corresponding to a transfer matrix $A^{(2)}$ is not in the focus is considered. In such a case, a part of the propagation distance of the terahertz wave pulse corresponding to the transfer matrix $A^{(2)}$ becomes longer than a part of the propagation distance corresponding to the transfer matrix $A^{(1)}$. If the physical property of each part is obtained by ignoring this effect, the physical property for the part corresponding to the transfer matrix $A^{(1)}$ and the part corresponding to the transfer matrix $A^{(2)}$ may be calculated to be a different result even for the same material. In the waveform reconstruction unit 113 according to this embodiment, in order to suppress this influence, a transfer matrix $C^{(m)}$ related to the following layer is used in combination with a transfer matrix $A^{(m)}$ as appropriate.

[Formula 16]

$$\begin{pmatrix} E_{(+)}(v) \\ E_{(-)}(v) \end{pmatrix} = C^{(m)} \begin{pmatrix} E'_{(+)}(v) \\ E'_{(-)}(v) \end{pmatrix} \tag{16}$$

$$= \begin{pmatrix} \exp[i(k_m d_m + \varphi_m)] & 0 \\ 0 & \exp[-i(k_m d_m + \varphi_m)] \end{pmatrix} \begin{pmatrix} E'_{(+)}(v) \\ E'_{(-)}(v) \end{pmatrix}$$

(16)

A difference with the transfer matrix $A^{(m)}$ is that the change in the secondary propagation distance of the terahertz wave pulse in time domain is represented as a phase change $\phi_m$ in the frequency domain. The phase change $\phi_m$ is represented by the following formula.

[Formula 17]

$$\varphi_m = \frac{2\pi v dL_m}{c} \tag{17}$$

An optical path length change of the terahertz wave pulse in the $m^{th}$ layer material is denoted by $dL_m$. The change dL in the secondary propagation distance of the entire terahertz wave pulse can be represented in a form to which the optical path length change $dL_m$ in each layer is added as in the following formula.

[Formula 18]

$$dL = \Sigma_{j=1}^{m} dL_j \tag{18}$$

The waveform reconstruction unit 113 refers to an output from the relative position monitoring unit 110 and calculates the change $dL_m$ in the secondary propagation distance of the terahertz wave pulse in each layer by using the data stored in the propagation distance database 111. The change $dL_m$ used in formula (17) can be selected as below depending on a condition of a material corresponding to the transfer matrix $C^{(m)}$. In a case where the material corresponding to the transfer matrix $C^{(m)}$ is already-known or can be assumed, the optical path length change of the terahertz wave pulse is obtained by using actually measured data measured in advance as in FIG. 10A.

[Formula 19]

$$dL_m = dL_{material\_m} \tag{19}$$

Here, $dL_{material\_m}$ is a value of a change in the secondary propagation distance of the terahertz wave pulse of an already-known or assumed material in the $m^{th}$ layer. A change $dL_{material\_m}$ in the secondary propagation distance of the terahertz wave pulse is calculated by the waveform reconstruction unit 113 by using information in the propagation distance database 111. It is preferred that the actually measured data be used as $dL_{material\_m}$ (that is, a measuring result of a material having the same physical property and the shape as the object to be measured). In a case where there is a significant difference between a measuring condition of the data in the propagation distance database 111 (for example, thickness of the material) and a measuring condition when analyzing by using the transfer matrix $C^{(m)}$, the following is possible. That is, as described above, it is also possible to use a value assumed from measured data under a plurality of measuring conditions stored in the propagation distance database 111 as $dL_{material\_m}$. By using the actual measured data, it is possible to increase a speed of optimization by limiting an amount of calculation by the waveform reconstruction unit 113 as well as to increase reliability of the apparatus.

Furthermore, in a case where a change in the secondary propagation distance in an atmosphere (free space) is used as data stored in the propagation distance database 111, $dL_m$ is represented by the following formula.

[Formula 20]

$$dL_m = \tilde{n}_m dL_{air\_m} \quad (20)$$

Here, $dL_{air\_m}$ represents a value of a change in the secondary propagation distance of the terahertz wave pulse for the $m^{th}$ layer material when the atmosphere (free space) is assumed. Practically, as described above, $dL_{air\_m}$ is calculated by using a thickness $d_m$ used in the transfer matrix $C^{(m)}$. The change in the secondary propagation distance of the terahertz wave pulse, being assumed by using a parameter of the transfer matrix output in a process of optimization, can be applied to materials in various forms. As a result, a universal use of the apparatus increases.

As described above, the transfer matrix $C^{(m)}$ is used in place of the transfer matrix $A^{(m)}$ in a part where a correction is necessary in the secondary propagation distance of the terahertz wave pulse. For example, measuring is performed in a state in which the object to be measured 108 having a two-layer structure is in close contact with the measuring window 201, and in a case where it is necessary to add the change in the secondary propagation distance of the terahertz wave pulse derived from an optical system of the apparatus by the measuring window 201, formula (14) is changed to a formula below.

[Formula 21]

$$M' = C^{(1)}B^{(1)}A^{(2)}B^{(2)}A^{(3)}B^{(3)} \quad (21)$$

Here, m=1 corresponds to the measuring window 201, and m=2, 3 corresponds to an inner structure of the object to be measured 108. Furthermore, in a case where the regressive wave from the material can be ignored such as in a case where the material has a large absorption or sufficient thickness, such as a living body, formula (15) is represented by the following formula.

[Formula 22]

$$\begin{pmatrix} E_{(+)} & (v) \\ E_{(-)} & (v) \end{pmatrix} = M \begin{pmatrix} E'_{(+)}(v) \\ 0 \end{pmatrix} \quad (22)$$

Furthermore, in a case where a boundary of the material can be regarded as a mirror surface reflecting the electromagnetic wave, formula (14) can be represented by the following formula. Here, the mirror surface exists in the $m^{th}$ layer.

[Formula 23]

$$M'' = A^{(1)}B^{(1)}A^{(2)}B^{(2)}A^{(3)}B^{(3)}\ldots A^{(m)} = (\Pi_{j=1}^{m-1} A^{(j)}B^{(j)}) A^{(m)} \quad (23)$$

A transfer matrix I (omitted, but exists after $A^{(m)}$ in formula (14)) is an identity matrix. By using this transfer matrix M'', formula (15) is represented by the following formula.

[Formula 24]

$$\begin{pmatrix} E_{(+)} & (v) \\ E_{(-)} & (v) \end{pmatrix} = M'' \begin{pmatrix} E'_{(+)} & (v) \\ E'_{(-)} & (v) \end{pmatrix} \quad (24)$$

Formula (24) means that the electromagnetic wave is completely reflected on a mirror surface of the material, whereby the progressive wave and the regressive wave are regarded as the same. As a result, an effect of the transfer matrix $B^{(m)}$ related to an interface of a part corresponding to the mirror surface is included by expressing as $E'_{(-)} = E'_{(+)}$, whereby the transfer matrix $B^{(m)}$ of the $m^{th}$ layer can be ignored.

By using the transfer matrix as above, the waveform reconstruction unit 113 performs the optimization of the transfer matrix, and calculates the reconstructed waveform $E_{rec}(t)$ approximated to the measurement waveform $E_{meas}(t)$. Specifically, a comparison is made between the measurement waveform $E_{meas}(t)$ and the reconstructed waveform $E_{rec}(t)$ by converting information on the frequency domain into the time domain. Here, an initial value of the transfer matrix is determined by referring to the physical property database 112. For example, in a case where a candidate of the physical property is selected, the physical property value thereof is input as the initial value. Furthermore, it is also possible to determine a range of each variable of the transfer matrix to be optimized by referring to the candidate material indicated in the physical property database 112. By undergoing such a process, it is possible to prevent each variable of the transfer matrix from converging on an abnormal value when the waveform reconstruction unit 113 calculates the reconstructed waveform $E_{rec}(t)$, whereby it is possible to increase reliability of the apparatus.

A display unit 114 is a part on which the calculation result is displayed upon receiving a calculation result of the waveform reconstruction unit 113. As a display method, a physical property of the object to be measured 108 is displayed by using the variable used in the calculation. Furthermore, it is also possible to specify the object to be measured 108 by comparing the physical property data stored in the physical property database 112 and the calculation result of the waveform reconstruction unit 113. Furthermore, in a case where the apparatus has an apparatus configuration to acquire a tomography image of the object to be measured 108, it is also possible to display by color-coding each physical property distributed over the tomography image. A display unit 114 is a part corresponding to a user interface structured so as to meet a request by a measurer, whereby the display configuration is not limited to this.

In the apparatus according to this embodiment, when the reconstructed waveform $E_{rec}(t)$ approximated to the measurement waveform $E_{meas}(t)$ measured by the apparatus is structured based on the physical property information of the reference waveform $E_{ref}(t)$ and the physical property database 112, the change dL in the propagation distance of the terahertz wave pulse is added. As a result, an accuracy of calculation of the reconstructed waveform $E_{rec}(t)$ is improved.

Figure 7:
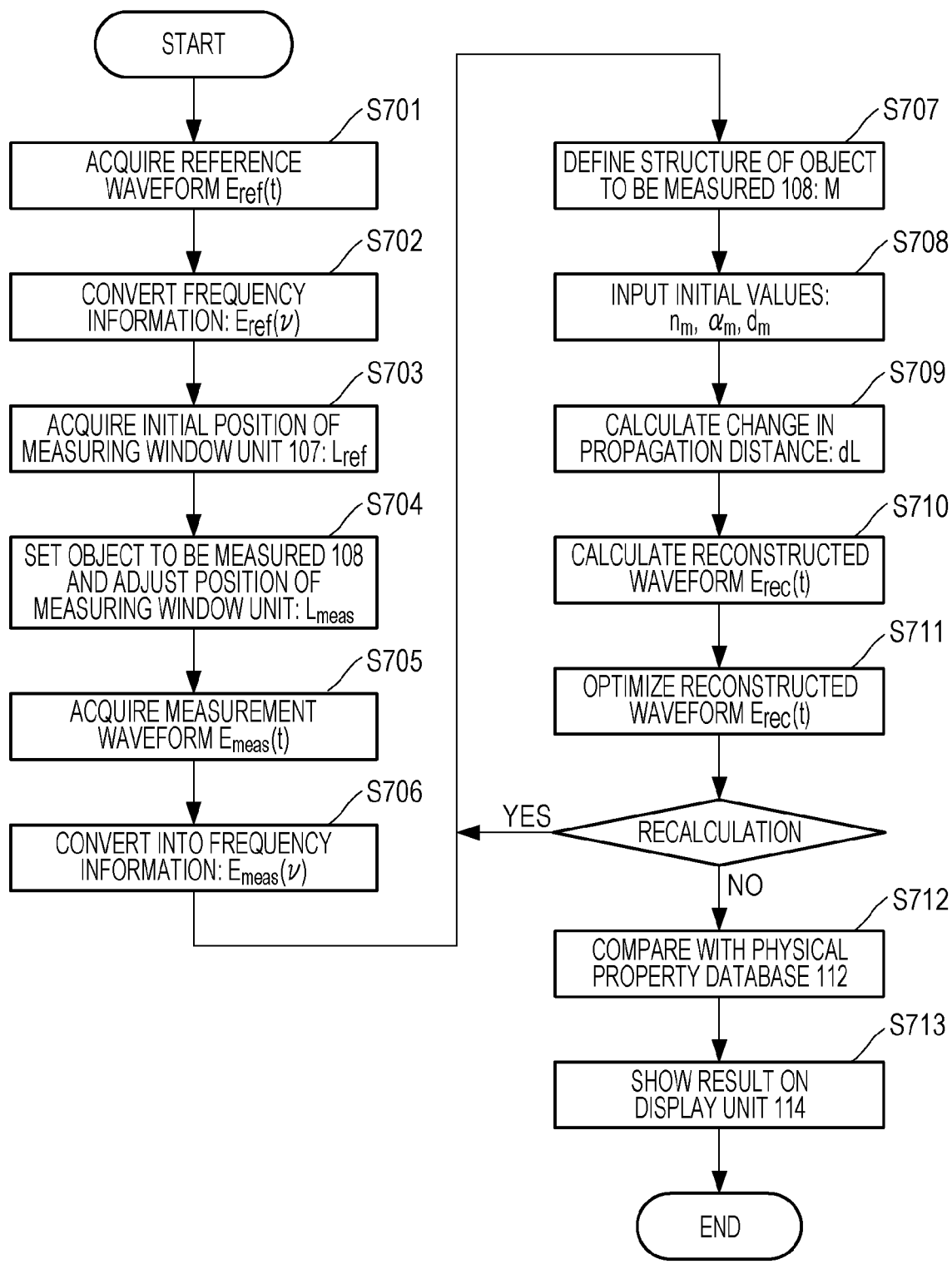
FIG. 7 is a flowchart illustrating an exemplary operational flow of an apparatus according to Embodiment 2.
Figure 8A:
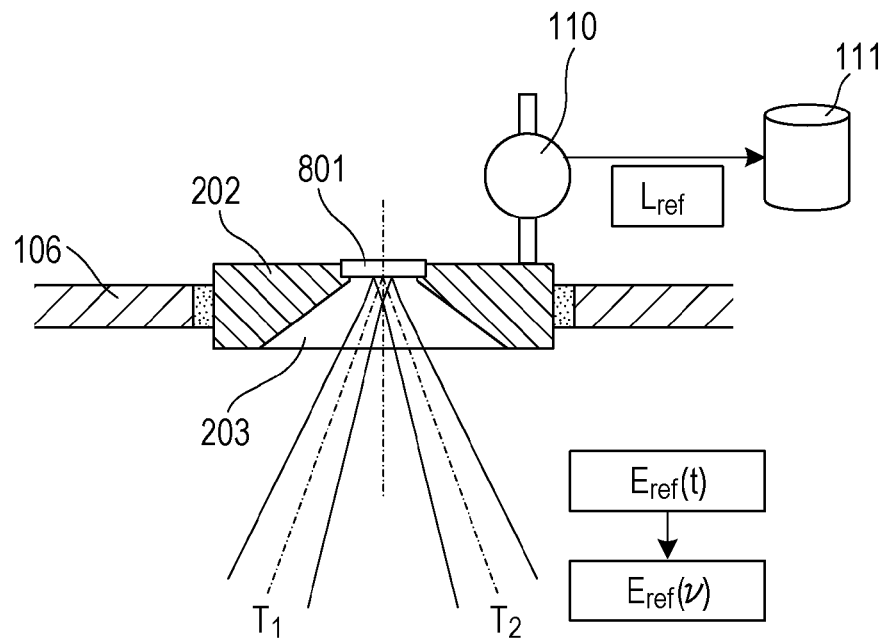
FIGS. 8A and 8B are views illustrating an operation of the apparatus according to Embodiment 2.
Figure 8B:
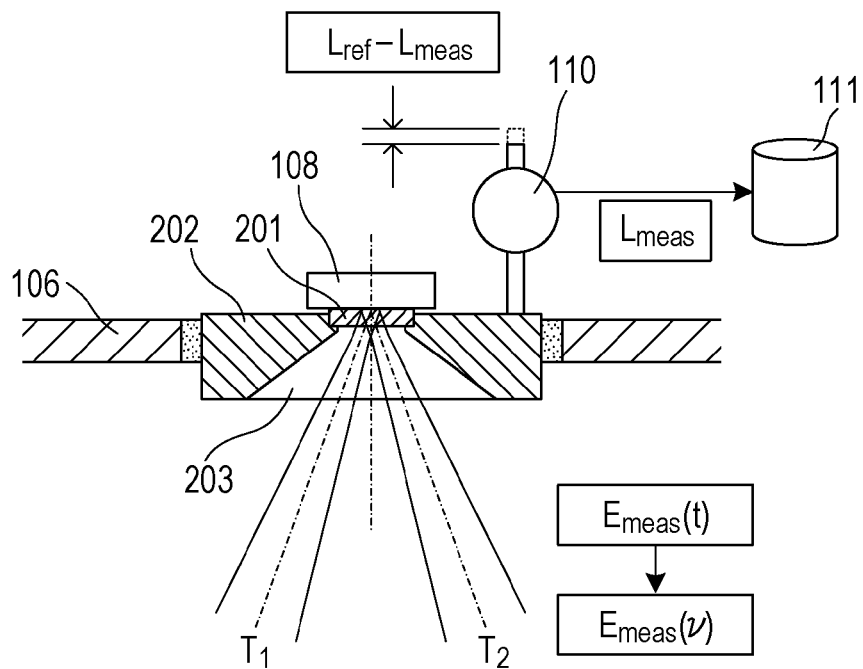

A method of this apparatus is described with reference to the drawings. FIG. 7 is a view illustrating an exemplary operational flow of this apparatus. FIGS. 8A and 8B are views illustrating an operation of this apparatus. When the apparatus starts the operation, the waveform acquisition unit 109 refers to an adjustment amount from the delay optical unit 104 and an output from the detecting unit 102, and acquires the reference waveform $E_{ref}(t)$ from the measuring window unit 107 (S701). The waveform acquisition unit 109 performs a Fourier conversion on the acquired reference waveform $E_{ref}(t)$, converts it into a frequency information $E_{ref}(v)$, and outputs it to the waveform reconstruction unit 113 (S702). At this time, as in FIG. 8A, the measuring window 201 constituting the measuring window unit 107 is replaced with a reflector 801, which reflects the terahertz wave pulse. Therefore, the terahertz wave pulse $T_1$ entering the reflector 801 and the terahertz wave pulse $T_2$ from the reflector 801 are the same. Furthermore, in FIG. 8A, a dial gauge is used as the relative position monitoring unit 110. In a case of monitoring a relative position in a non-contact manner, a laser displacement system and the like can be applied. The relative position monitoring unit 110 outputs a position of the measuring window unit 107 (a position of the measuring window casing 202 in an example in FIG. 8A) when the reference waveform $E_{ref}(t)$ is acquired as an initial position $L_{ref}$ of the measuring window unit 107 to a propagation distance database 111 (S703). It is not necessary to measure data obtained in steps S701 to S703 for each measuring operation, but instead it may be acquired in advance.

As in FIG. 8B, the measuring window 201 is installed in the measuring window unit 107 in place of the reflector 801. Then, the object to be measured 108 is disposed on an opposite side of the propagation path of the terahertz wave pulse relative to the measuring window unit 107. Specifically, the object to be measured 108 is disposed in a close contact with the measuring window 201. As a result, the terahertz wave pulse $T_2$ becomes a time waveform to which the information from the measuring window 201 and the object to be measured 108 is added. The measurer, according to a form and a character of the measuring window 201 and a place to observe in the object to be measured 108, adjusts a focal position of the terahertz wave pulse $T_1$. Specifically, in case of FIG. 8B, by adjusting a position of the measuring window casing 202, which constitutes the measuring window unit 107, the focal position of the terahertz wave pulse $T_1$ relative to the measuring window 201 and the object to be measured 108 can be adjusted. The relative position monitoring unit 110 outputs a position $L_{meas}$ of the measuring window unit 107 (a position of the measuring window casing 202 in an example in FIG. 8B), in which the focal position of the terahertz wave pulse $T_1$ has been adjusted, to the propagation distance database 111 (S704). An amount of change in the propagation distance of the terahertz wave pulse accompanied by a move of the measuring window unit 107 can be converted based on $L_{ref}-L_{meas}$ and information on an angle of incidence of the terahertz wave pulse $T_1$.

The waveform acquisition unit 109 refers to the adjustment amount of the delay optical unit 104 and the output from the detecting unit 102, and acquires a measurement waveform $E_{meas}(t)$ from the object to be measured 108 through the measuring window 201 (S705). The waveform acquisition unit 109 performs a Fourier conversion on the acquired measurement waveform $E_{meas}(t)$, converts it into a frequency information $E_{meas}(v)$, and outputs it to the waveform reconstruction unit 113 (S706). In structuring the reconstructed waveform $E_{rec}(t)$, the waveform reconstruction unit 113 defines a structure of the object to be measured 108 (S707). More specifically, the measuring window 201 and the object to be measured 108 are regarded as one measurement object, and a transfer matrix M used by the waveform reconstruction unit 113 is defined. The waveform reconstruction unit 113, for a parameter of each transfer matrix, acquires a parameter of an already-known part from the physical property database 112 (S708). Here, in a case where the parameter to use is not an already-known one, but a material thereof is narrowed down to a certain extent, it is also possible to set a parameter region by referring to the physical property database 112. In a case where a physical property constituting the measurement object is unknown, the measurer sets an initial value of an unknown parameter.

The waveform reconstruction unit 113 refers to position information of the measuring window unit 107 output from the relative position monitoring unit 110, and calculates the change dL in the secondary propagation distance of the terahertz wave pulse (S709). Then, the waveform reconstruction unit 113, by using each parameter of the transfer matrix, calculates the reconstructed waveform $E_{rec}(t)$ in a time domain (S710). Then, the waveform reconstruction unit 113, using the measurement waveform $E_{meas}(t)$ as a comparison target, optimizes the reconstructed waveform $E_{rec}(t)$ by using the reference waveform $E_{ref}(t)$, the change dL in the secondary propagation distance, and a physical property value (S711). Specifically, each parameter of the transfer matrix used in reconfiguration of the waveform is optimized.

In a case where the apparatus or the measurer determines that optimization calculation of the reconstructed waveform $E_{rec}(t)$ is necessary again, the process returns to S707 again. For example, in a case where a degree of agreement between the measurement waveform $E_{meas}(t)$ and the reconstructed waveform $E_{rec}(t)$ is low, and where it is necessary to try a transfer matrix M having a different structure, a recalculation is performed. Furthermore, a recalculation is tried in a case where an abnormal value is included in a calculation result of the transfer matrix.

According to this method, in optimizing the reconstructed waveform $E_{rec}(t)$, the change dL in the secondary propagation distance of the terahertz wave pulse is considered in the optimization. As a result, an accuracy of the optimization of the reconstructed waveform $E_{rec}(t)$ improves.

In a case where the object to be measured 108 is compared by using each parameter of the calculated transfer matrix, a substance constituting the object to be measured 108 is determined by comparing a physical property value used in structuring the reconstructed waveform $E_{rec}(t)$ and a physical property value of a substance stored in the physical property database 112 (S712). According to this method, the physical property value is obtained from the reconstructed waveform $E_{rec}(t)$ considering the change dL in the secondary propagation distance of the terahertz wave pulse. Therefore, compared to a configuration in which the change dL in the secondary propagation distance is not considered, an accuracy of the obtained physical property value improves. As a result, accuracy in determining a substance constituting the object to be measured 108 by comparing the physical property value improves. That is, accuracy in determining a substance constituting the object to be measured by comparing the physical property value used in structuring the reconstructed waveform and information on the physical property of the substance stored in the physical property database improves.

A result output in the above process is presented to the measurer by the display unit 114 (S713). Note, however, that in the descriptions above, the time waveform of the terahertz wave pulse $T_2$ obtained in the waveform acquisition unit 109 and in the waveform reconstruction unit 113 is equivalent to a tomography image of an A scan. In this embodiment, in a case where a tomography image of a B scan (tomography image) or a three-dimensional tomography image is to be acquired, it can be realized by scanning the object to be measured 108 with the terahertz wave pulse $T_1$. Specifically, these images can be realized by scanning a surface having a vector in a normal line direction relative to the moving direction of the measuring window unit 107 with the terahertz wave pulse $T_1$ in a one-dimensional direction or a two-dimensional direction. On the display unit 114, these images are also displayed.

Figure 11A:
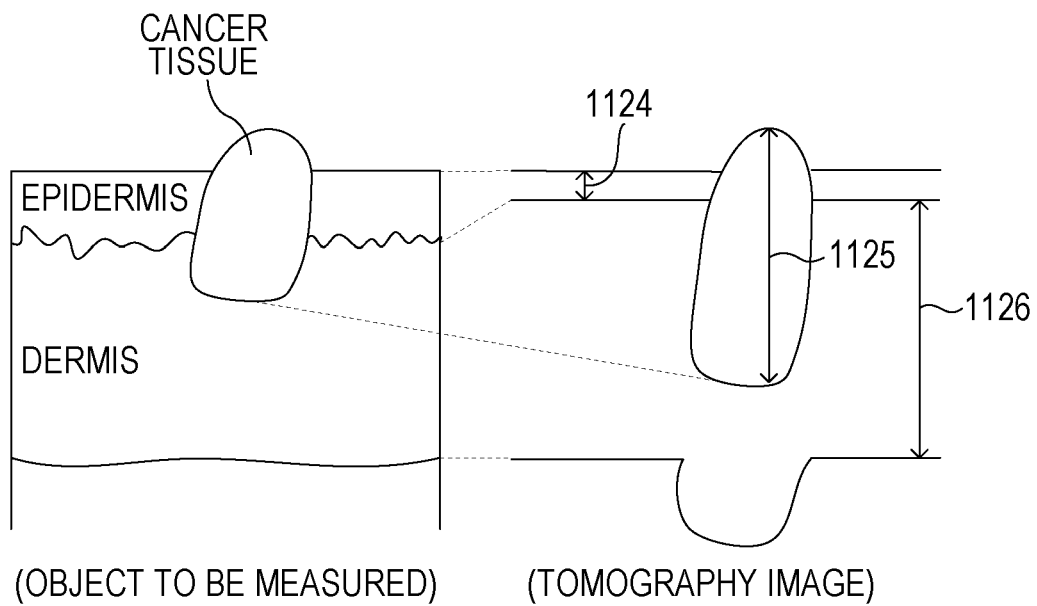
FIGS. 11A and 11B are views illustrating an exemplary display method of a display unit according to Embodiment 2.
Figure 11B:
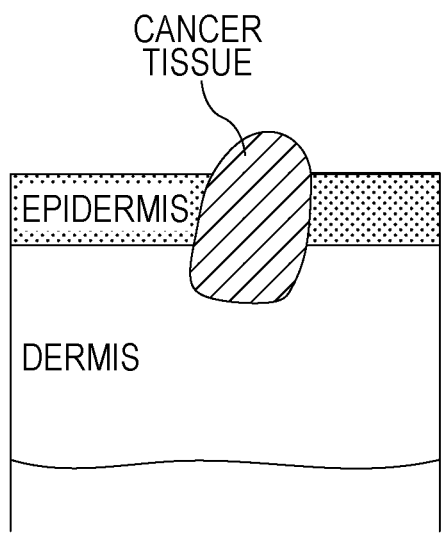

FIG. 11A is a schematic view of the object to be measured and a tomography image thereof. Here, a tomography image of a B scan is illustrated. When the time waveform acquired from the waveform acquisition unit 109 is visualized, the propagation speed of the terahertz wave pulse changes due to a difference in a physical property of each region constituting the object to be measured, whereby a propagation length of the terahertz wave pulse in each region becomes different. FIGS. 11A and 11B illustrate an exemplary skin including a cancer tissue, an epidermis, and a dermis as the object to be measured. As a result, when information of the waveform acquisition unit 109 is visualized, as a tomography image in FIG. 11A, a position of the interface partly changes compared to a sectional structure of the object to be measured. At this time, in the waveform reconstruction unit 113, by defining a first feature region 1124, a second feature region 1125, and a third feature region 1126 as structures of the object to be measured 108, and by performing optimization of the transfer matrix, a physical property of each region can be determined. Here, in FIGS. 11A and 11B, as a feature region, an outermost surface of the epidermis and a region sandwiched by an interface of the epidermis and the dermis is referred to as the first feature region 1124. Furthermore, a region sandwiched by an outermost surface of the cancer tissue and an interface of the cancer tissue and the dermis is referred to as the second feature region 1125. Furthermore, a region sandwiched by an interface of the epidermis and the dermis, and an interface of the dermis and a subcutaneous tissue is referred to as the third feature region 1126. In the display unit 114, as in FIG. 11B, by referring to the physical property of each feature region, a size of each feature region of the tomography image is adjusted, and an image close to the object to be measured is acquired. At this time, a display form of the feature region is changed according to the physical property of each feature region. For example, it is possible to change the color for each feature region.

(Embodiment 3)

Another embodiment with which an idea of the present invention can be carried out is described herein with reference to the drawings. Specifically, it is a modification of the measuring window unit 107. Note that a description is omitted for any part common with the descriptions above.

The measuring window unit 107 described in Embodiment 1 is an embodiment in which the measuring window 201 is fixed to the measuring window casing 202 constituting the measuring window unit 107. Accordingly, as in Embodiment 2, in order to acquire a multidimensional tomography image, it is necessary to scan the object to be measured 108 placed on the measuring window 201 with the terahertz wave pulse $T_1$. Unlike such embodiment, in this embodiment, there is provided a measuring window unit 107 with which a multidimensional tomography image can be acquired by moving an object to be measured 108 itself placed on the measuring window unit 107.

Figure 4:
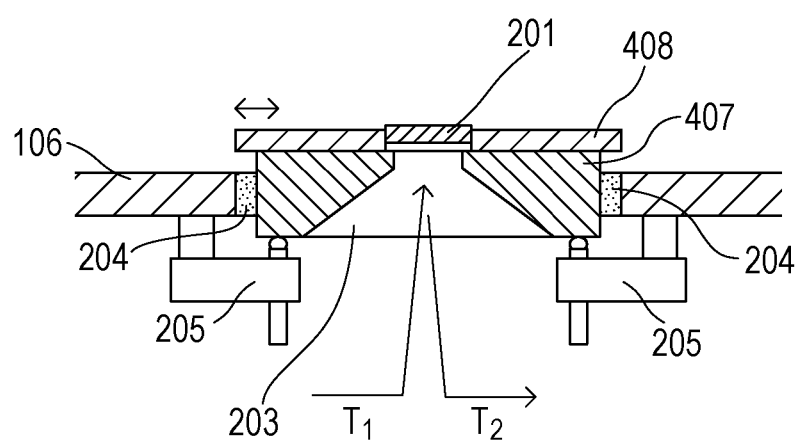
FIG. 4 is a view illustrating a measuring window unit according to a modification of Embodiment 3.

FIG. 4 is a configuration of the measuring window unit 107 according to this embodiment. A difference from the configuration of the measuring window unit 107 described above is that a measuring window casing 202 includes a first measuring window casing 407 and a second measuring window casing 408. The first measuring window casing 407 is a part for moving the measuring window 201 in a direction to change a propagation distance of a terahertz wave pulse. In FIG. 4, the first measuring window casing 407 is supported by an actuator 205; however, as described in FIGS. 3A to 3C of Embodiment 1, it may also be a configuration in which it is supported by an extensible part 306 or a guide screw 308. In such a case, the first measuring window casing 407 is moved by an actuator 305 provided outside the casing 106. The second measuring window casing 408 supports the measuring window 201, and is disposed above the first measuring window casing 407. The second measuring window casing 408 is scanned by a stage, not illustrated, in a one-dimensional direction or two-dimensional direction on a surface having a vector in a normal line direction relative to a direction in which the propagation distance of the terahertz wave pulse changes. Accordingly, the multidimensional tomography image such as a scanned tomography image (tomography image) and a three-dimensional tomography image can be acquired. Note, however, that the stage, not illustrated, described here may also serve as the actuator 305 illustrated in FIGS. 3A to 3C. Specifically, a part of the stage, not illustrated, is configured to include the second measuring window casing 408, and the stage can move in a moving direction of the measuring window unit 107 and in a direction of a surface having a vector in a normal line direction relative to the moving direction of the measuring window unit 107.

Figure 13A:
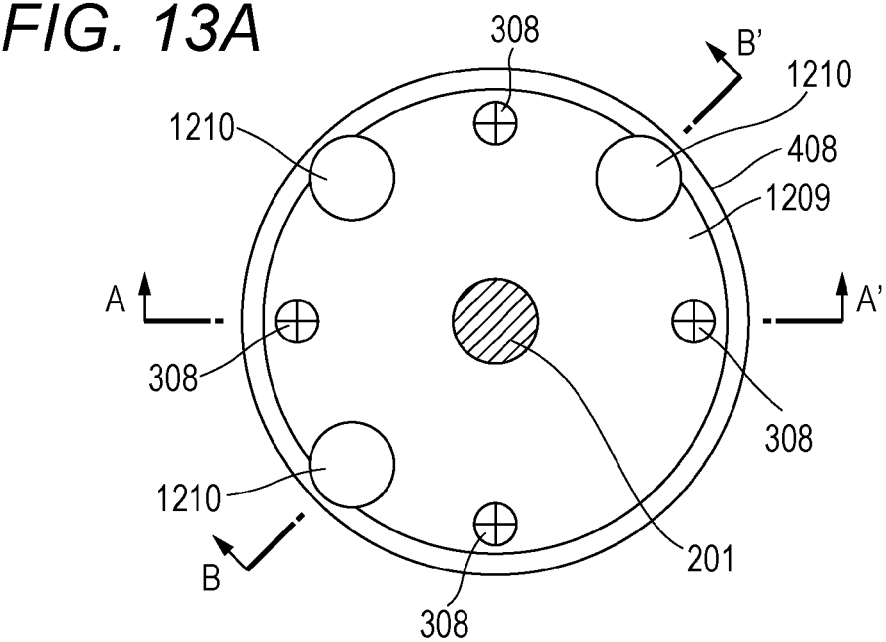
FIGS. 13A, 13B and 13C are views illustrating a modification of a measuring window unit according to Embodiment 3.
Figure 13B:
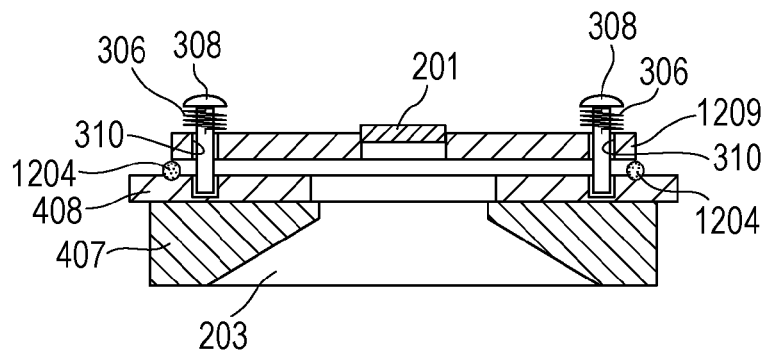
Figure 13C:
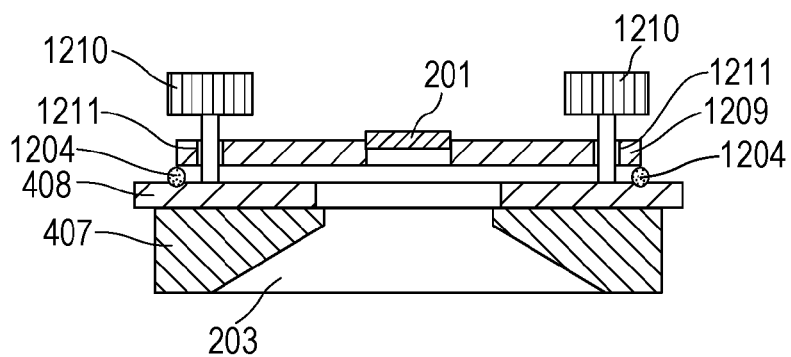

FIGS. 13A, 13B and 13C illustrate a further modification of the measuring window unit 107 described in this embodiment. In the measuring window unit 107 in FIGS. 13A to 13C, the inclination adjustment plate 1209 illustrated in FIGS. 12A to 12C is disposed above the second measuring window casing 408. Accordingly, the measuring window unit 107 can adjust an inclination of the measuring window 201.

The measuring window 201 according to this embodiment is scanned in a one-dimensional direction or a two-dimensional direction on a surface having a vector in a normal line direction relative to a direction in which the propagation distance of the terahertz wave pulse changes. As a result, the measuring point relatively moves relative to a terahertz wave pulse, whereby a multidimensional tomography image can be acquired. Due to the moving of the measuring window 201, a moving mechanism of the measuring point can be disposed outside the casing 106 of the apparatus by realizing moving of the measuring point of the terahertz wave pulse. As a result, an internal volume of the casing 106 can be made smaller, and the time necessary for adjusting the measuring environment can be reduced. Accordingly, miniaturization of the apparatus and stabilization of the measuring environment become easier.

(Embodiment 4)

Another embodiment with which an idea of the present invention can be carried out is described herein with reference to the drawings. Specifically, the mechanism of the measuring window unit 107 described above is applied to a generating unit 101 and a detecting unit 102. Note that a description is omitted for any part common with the descriptions above.

Figure 5A:
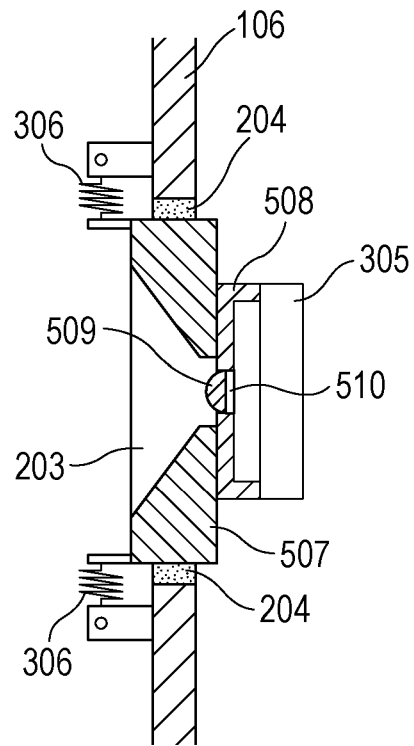
FIG. 5A is a view illustrating a measuring window unit for holding an element according to Embodiment 4.
Figure 5B:
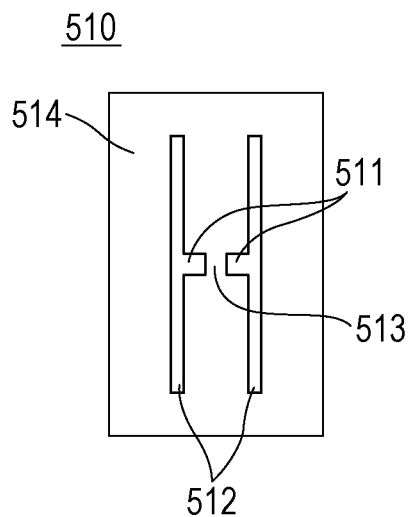
FIG. 5B is an exemplary configuration of an element.

FIG. 5A is a view illustrating a structure of the measuring window unit 107 according to this embodiment. A measuring window 509 is a member for collecting a terahertz wave pulse to an element 510. In many cases, a hemispherical lens and a hyper-hemispherical lens can be applied. The element 510 is disposed so as to closely contacting the measuring window 509. FIG. 5B is an exemplary configuration of the element 510. As shown in FIG. 5B, the element 510 is an element in which an antenna electrode 511 and a feeding electrode 512 are formed on a semiconductor substrate 514. This element is also referred to as a photoconductive element. As the semiconductor substrate 514, for example, a low-temperature grown gallium arsenide (LT-GaAs) and indium gallium arsenide (LT-InGaAs) can be applied. A material of the semiconductor substrate 514 is not limited to these, and an already-known material that can generate or detect the terahertz wave can be applied. A shape and a size of the antenna electrode 511 and the feeding electrode 512 are designed as appropriate according to a wavelength and a spectrum shape of the terahertz wave pulse to be used. For the hemispherical lens and the hyper-hemispherical lens, a material having a small loss and dispersion to the terahertz wave is preferred. For example, high resistance silicon can be applied. Note that the material is not limited to these as long as the element can generate and detect the terahertz wave.

In FIG. 5A, the measuring window 509 is supported by a second measuring window casing 508. Then, a first measuring window casing 507 is supported by the extensible part 306 to the casing 106. Furthermore, the first measuring window casing 507 and the second measuring window casing 508 are disposed in a close contact with each other. As described in Embodiment 3, the first measuring window casing 507 is a part for moving the measuring window 509 and the element 510 in a direction in which the propagation distance of the terahertz wave pulse changes. The second measuring window casing 508 is a part for moving the measuring window 509 and the element 510 in a one-dimensional direction or a two-dimensional direction for a surface having a vector in a normal line direction relative to a direction in which the propagation distance of the terahertz wave pulse changes. To the second measuring window casing 508, an actuator 305 is connected as illustrated, and a force for moving the first measuring window casing 507 and the second measuring window casing 508 is applied.

In the above configuration, a position of the element 510 can be adjusted through the measuring window unit 107. Note that the measuring window 509 in a configuration in FIG. 5A is not always necessarily, and the element 510 may also serve as the measuring window 509. In a configuration according to this embodiment, either or both of the generating unit and the detecting unit are disposed on an opposite side of the propagation path of the electromagnetic wave pulse inside a casing relative to the casing. In this way, since at least one of the generating unit 101 and the detecting unit 102 can be disposed outside the casing 106, the internal volume of the casing 106 can be made smaller. As a result, the time necessary for adjusting an ambient atmosphere inside the casing 106 can be reduced, and miniaturization of the apparatus becomes easier.

(Embodiment 5)

Another embodiment with which an idea of the present invention can be carried out is described herein with reference to the drawings. Specifically, it is a modification of the apparatus described in Embodiment 1, and a configuration in which this apparatus is made into a probe is disclosed. That is, this embodiment is the probe for measuring the object to be measured further having a waveguide part for waveguiding an electromagnetic wave pulse, and the probe is provided with a measuring window at an edge thereof. Note that a description is omitted for any part common with the descriptions above.

Figure 6A:
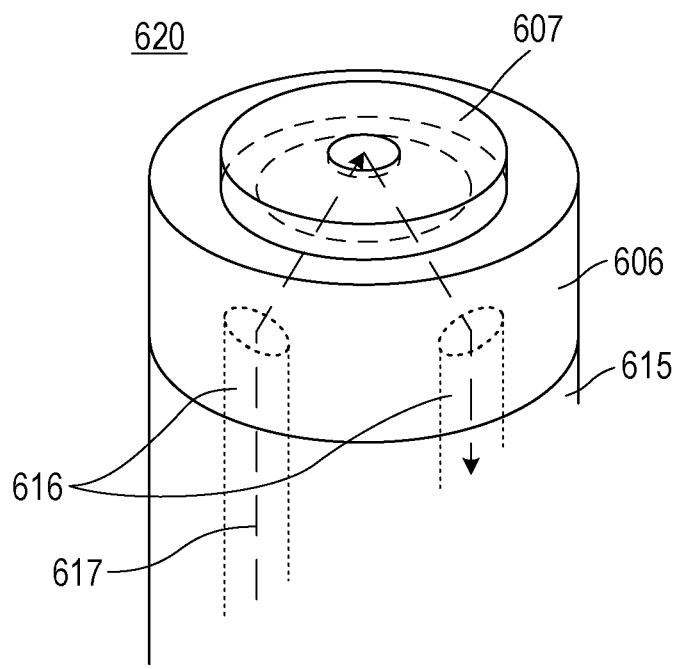
FIGS. 6A to 6C are views illustrating a probe configuration according to Embodiment 5.
Figure 6B:
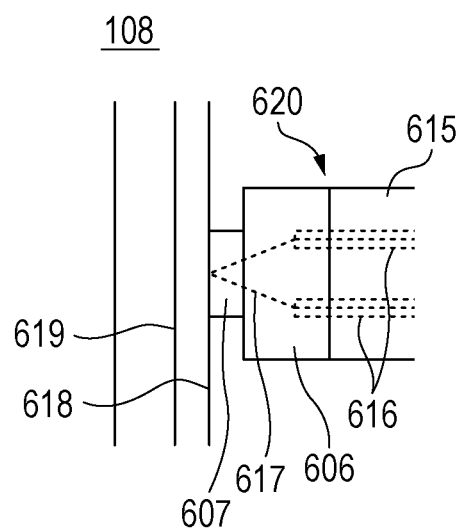
Figure 6C:
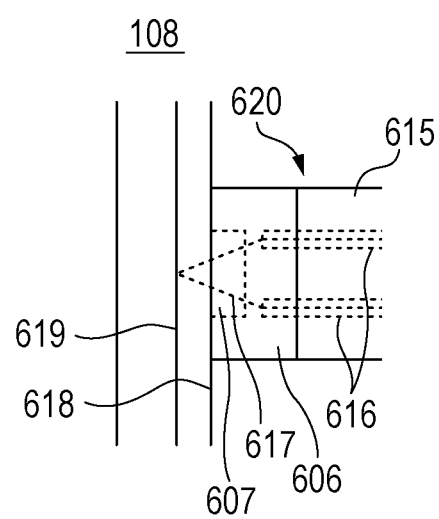

FIGS. 6A to 6C illustrate a configuration of the apparatus made into a probe according to this embodiment. FIG. 6A is a view illustrating a configuration of a tip part of a probe 620. The tip part of the probe 620 includes a measuring window unit 607, a casing 606, and a covered section 615. The measuring window unit 607 has the same configuration as the ones described in the above embodiments. Note, however, that a material constituting the measuring window unit 607 is selected as appropriate according to a use environment of the probe 620. As described above, an adjustment of the position of the measuring window unit 607 may be performed by an actuator disposed inside the casing 606 or by pressing the probe 620 itself against the object to be measured 108 as illustrated in FIGS. 6B and 6C. FIG. 6B is a configuration in which a focus of the terahertz wave pulse $T_1$ is adjusted to the first interface 618 relative to the object to be measured 108 having the first interface 618 and a second interface 619. In such a state, in a case where the focal position of the terahertz wave pulse $T_1$ is adjusted to the second interface 619, as in FIG. 6C, the measuring window unit 607 is moved inside the casing 606 in a process where the probe 620 is pressed against the object to be measured 108. Accordingly, moving of the focus of the terahertz wave pulse $T_1$ becomes possible.

The casing 606 includes a material strong enough for supporting the measuring window unit 607. In a case where a covered section 615 has sufficient strength and rigidity, the covered section 615 may also serve as the casing 606.

As illustrated in FIGS. 6A to 6C, the covered section 615 contains a waveguide part 616, which waveguides the terahertz wave pulse. As the waveguide part 616, an already-known waveguide configuration can be applied. For example, a coaxial waveguide or a hollow fiber can be applied. It is preferred that a material constituting the waveguide part 616 have loss and dispersion, which are as small as possible, relative to the terahertz wave. FIG. 6A is an example in which a propagation direction of the terahertz wave pulse is adjusted depending on a shape of a tip of the waveguide part 616. Note, however, that the adjustment of the propagation direction of the terahertz wave pulse is not limited to this configuration, and an optical element (such as a mirror or a lens) disposed inside the casing 606 inside may also be used.

The apparatus according to this embodiment is provided with the measuring window unit 607 at the tip of the probe 620, whereby the focal position of the terahertz wave focused on a surface of or inside the object to be measured 108 contacting the measuring window unit 607 can be varied. As a result, the focal position can be easily moved to a position to measure the object to be measured 108, whereby a structural observation of the object to be measured 108 can be accurately performed.

An aspect of the present invention is also a method of acquiring information on a surface or an inner structure of the object to be measured placed on the measuring window, which is movably provided in a casing for adjusting an ambient atmosphere surrounding the propagation path and including at least a part of the propagation path of the electromagnetic wave pulse, by using an electromagnetic wave pulse.

The method includes the above-described steps: a step of generating an electromagnetic wave pulse; a step of acquiring a reference waveform of the electromagnetic wave pulse from the measuring window, which is irradiated with the electromagnetic wave pulse; a step of acquiring a measurement waveform of the electromagnetic wave pulse from the object to be measured, which is irradiated with the electromagnetic wave pulse; a step of acquiring information on a physical property of a substance used for structuring a reconstructed waveform from the physical property database; a step of calculating a change in the secondary propagation distance in the electromagnetic wave pulse based on information of a relative position between the focal position of the electromagnetic wave pulse and the measuring window; and a step of structuring and optimizing the reconstructed waveform by using the reference waveform, the change in the secondary propagation distance, and the physical property information, by comparing with the measurement waveform.

Other Embodiments

Embodiments of the present invention can also be realized by a computer of a system or apparatus that reads out and executes computer executable instructions recorded on a storage medium (e.g., non-transitory computer-readable storage medium) to perform the functions (e.g., the algorithm of FIG. 7) of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

As described above, according to embodiments of the present invention, the apparatus uses the measuring window, which is movable relative to the casing including at least a part of the propagation path of the electromagnetic wave pulse, an adjustment of the focal position of the terahertz wave and a position of the object to be measured becomes possible in a state in which a fluctuation of an ambient atmosphere inside the casing is suppressed. As a result, an accurate observation of the physical property or the structure of the object to be measured becomes possible, whereby the reliability in measuring improves.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-012174, filed Jan. 25, 2013, which is hereby incorporated by reference herein in its entirety.

What is claimed is:

1. An apparatus configured to acquire information on an object to be measured by irradiating the object with an electromagnetic wave pulse, the apparatus comprising:
   a generating unit configured to generate the electromagnetic wave pulse with which the object is irradiated;
   a detecting unit configured to detect the electromagnetic wave pulse from the object; and
   a casing including a propagation path of the electromagnetic wave pulse leading from the generating unit to the detecting unit and a measuring window interposed between the propagation path and the object,
   wherein the measuring window is formed of a material that has a transmittance to a terahertz wave and is configured to suppress fluctuation of ambient atmosphere in the casing, and
   wherein a distance of the propagation path is changed by moving the measuring window contacted from outside of the casing by the object, in a state in which the fluctuation of the ambient atmosphere is suppressed.

2. The apparatus according to claim 1, wherein at least one of the generating unit and the detecting unit is disposed toward inside the casing from outside of the casing.

3. The apparatus according to claim 1, wherein the measuring window unit has an inclination adjustment mechanism configured to adjust an inclination of the measuring window.

4. The apparatus according to claim 1, further comprising:
   a waveform acquisition unit configured to acquire a time waveform of the electromagnetic wave pulse by referring to output from the detecting unit;
   a relative position monitoring unit configured to monitor a relative position of the focal position of the electromagnetic wave pulse and the measuring window unit;
   a distance database configured to output information used for acquiring a change in a secondary distance of the propagation path caused by a change in an arrangement of an optical system existing in the propagation path, relative to the relative position;
   a physical property database in which a substance identification name and physical property information of the substance are stored;
   a waveform reconstruction unit configured to structure a reconstructed waveform approximated to a measurement waveform of the electromagnetic wave pulse from the object by using a reference waveform acquired in the waveform acquisition unit of the electromagnetic wave pulse from the measuring window, a change in the secondary distance, and information on physical property stored in the physical property database.

5. The apparatus according to claim 1, further comprising:
   a waveguide part configured to function as a probe for measuring the object, and to waveguide the electromagnetic wave pulse,
   wherein the probe has the measuring window unit at a tip thereof.

6. The apparatus according to claim 1, wherein the electromagnetic wave pulse is a terahertz wave pulse having a component of any frequency band in a range of 0.03 THz to 30 THz.

7. A method of acquiring information on an object to be measured by irradiating the object with an electromagnetic wave pulse, the method comprising:
   generating the electromagnetic wave pulse with a generating unit and irradiating the object with the electromagnetic wave pulse;
   detecting the electromagnetic wave pulse from the object with a detecting unit;
   enclosing a propagation path of the electromagnetic wave pulse leading from the generating unit to the detecting unit in a casing having a measuring window interposed between the propagation path and the object, such that the electromagnetic wave pulse transmits through the measuring window in traveling from the generating unit to the object and from the object to the detecting unit;
   changing a distance of the propagation path by moving the measuring window contacted from outside of the casing by the object, in a state in which fluctuation of ambient atmosphere in the case is suppressed by the measuring window;
   acquiring a reference waveform of the electromagnetic wave pulse from the measuring window irradiated with the electromagnetic wave pulse;
   acquiring a measurement waveform of the electromagnetic wave pulse from the object irradiated with the electromagnetic wave pulse;
   acquiring information on a physical property of a substance used for structuring a reconstructed waveform from a physical property database;
   acquiring a change in a secondary propagation distance in the electromagnetic wave pulse from information on a relative position between a focal position of the electromagnetic wave pulse and the measuring window; and structuring and optimizing the reconstructed waveform by using the reference waveform, the change in the secondary propagation distance, and the information on the physical property, by comparing with the measurement waveform.

8. The method according to claim 7, further comprising:
determining a substance constituting the object by comparing a physical property value used in structuring the reconstructed waveform and the information on the physical property of a substance stored in the physical property database.

9. The method according to claim 7, wherein
the electromagnetic wave pulse is a terahertz wave pulse having a component of any frequency band in a range of 0.03 THz to 30 THz.

10. A non-transitory computer-readable storage medium storing thereon a program configured to cause a computer to control an apparatus configured to acquire information on an object to be measured by irradiating the object with an electromagnetic wave pulse, the apparatus including a generating unit to generate the electromagnetic wave pulse with which the object is irradiated, a detecting unit to detect the electromagnetic wave pulse from the object, and a casing including a propagation path of the electromagnetic wave pulse leading from the generating unit to the detecting unit and a measuring window interposed between the propagation path and the object, the program including executable-instructions to execute steps comprising:

changing a distance of the propagation path by moving the measuring window contacted from outside of the casing by the object, in a state in which fluctuation of ambient atmosphere in the case is suppressed by the measuring window;

acquiring a reference waveform of the electromagnetic wave pulse from the measuring window irradiated with the electromagnetic wave pulse;

acquiring a measurement waveform of the electromagnetic wave pulse from the object irradiated with the electromagnetic wave pulse;

acquiring information on a physical property of a substance used for structuring a reconstructed waveform from a physical property database;

acquiring a change in a secondary propagation distance in the electromagnetic wave pulse from information on a relative position between a focal position of the electromagnetic wave pulse and the measuring window; and structuring and optimizing the reconstructed waveform by using the reference waveform, the change in the secondary propagation distance, and the information on the physical property, by comparing with the measurement waveform.

11. The apparatus according to claim 1, wherein the measuring window is formed of a terahertz transparent material including resin, silicone, quartz or diamond.

12. The apparatus according to claim 1, wherein the measuring window is formed of a resin material in a porous form.

13. The apparatus according to claim 1, wherein the measuring window is formed to be flat.

14. The apparatus according to claim 1, wherein the measuring window is formed to be flat such that scattering of the terahertz wave pulse is suppressed by the measuring window.

15. The apparatus according to claim 1, wherein the measuring window is formed to be flat to have a flatness of $1/100\lambda$ to $1/20\lambda$, where $\lambda$ is a center wavelength of the electromagnetic wave pulse.

* * * * *